US012781253B2

(12) United States Patent
Wu et al.

(10) Patent No.: US 12,781,253 B2
(45) Date of Patent: Nov. 3, 2026

(54) RECONSTRUCTED TAMARIND SEED POLYSACCHARIDE (TSP), AND PREPARATION METHOD AND USE THEREOF

(71) Applicant: Shanghai Jiao Tong University, Shanghai (CN)

(72) Inventors: Yan Wu, Shanghai (CN); Xianbao Sun, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 445 days.

(21) Appl. No.: 18/374,894

(22) Filed: Sep. 29, 2023

(65) Prior Publication Data

US 2024/0368652 A1 Nov. 7, 2024

(30) Foreign Application Priority Data

May 4, 2023 (CN) ......................... 202310491303.7

(51) Int. Cl.
*C12P 19/04* (2006.01)
*C12P 19/14* (2006.01)
*C12P 19/20* (2006.01)

(52) U.S. Cl.
CPC ............... *C12P 19/04* (2013.01); *C12P 19/14* (2013.01)

(58) Field of Classification Search
CPC ................................ C12P 19/04; C12P 19/14
See application file for complete search history.

(56) References Cited

PUBLICATIONS

Sun et al., International Journal of Biological Macromolecules, 252, 1-11, 2023.*
Zhang et al., Food Hydrocolloids, 155, 1-14, 2024.*

* cited by examiner

*Primary Examiner* — Maryam Monshipouri
(74) *Attorney, Agent, or Firm* — Reising Ethington P.C.

(57) ABSTRACT

The present disclosure belongs to the technical field of antifreezes, and relates to a reconstructed tamarind seed polysaccharide (TSP), and a preparation method and use thereof. In the present disclosure, a natural TSP is used as raw material. Depolymerization by cellulase unfolds dense self-aggregating coils of the natural TSP to form highly-solvated depolymerized long chains. A certain amount of strongly hydrophilic side-chain galactose is removed by β-galactosidase, and a local hydrophilic-hydrophobic ratio is adjusted to drive the assembly of depolymerized polysaccharide chains, thus forming a large-sized fibrous supramolecular structure. In this way, surface properties and an interface size effect of the reconstructed TSP participating in an ice crystal interaction are significantly improved, such that an ice recrystallization inhibition activity is significantly improved compared with that of the natural TSP. The reconstructed TSP breaks through objective limitation of a weak activity of the natural TSP-based ice recrystallization inhibitors.

6 Claims, 26 Drawing Sheets

RECONSTRUCTED TAMARIND SEED POLYSACCHARIDE (TSP), AND PREPARATION METHOD AND USE THEREOF

CROSS REFERENCE TO RELATED APPLICATION

This patent application claims the benefit and priority of Chinese Patent Application No. 2023104913037, filed with the China National Intellectual Property Administration on May 4, 2023, the disclosure of which is incorporated by reference herein in its entirety as part of the present application.

TECHNICAL FIELD

The present disclosure belongs to the technical field of antifreezes, and in particular relates to a reconstructed tamarind seed polysaccharide (TSP), and a preparation method and use thereof.

BACKGROUND

Ice recrystallization is mainly an energy-driven Ostwald ripening process, in which small ice crystals with higher energy gradually disappear while large ice crystals continue to grow. The large ice crystals formed due to the ice recrystallization during frozen storage of food, especially under temperature fluctuations, seriously affect the quality, functionality, and consumer acceptance of products. Therefore, the effective inhibition of ice recrystallization is crucial to the development of high-quality frozen foods.

Traditional small-molecule antifreezes such as sucrose and sorbitol have a certain antifreeze effect. However, due to a sweet taste or high calorie, these antifreezes do not conform to the consumption concept of healthy food and are not suitable for the application of non-sweet food. Antifreeze proteins from natural sources have been proven to show an excellent ice recrystallization inhibition ability in food, but are challenged by few sources, high production costs, and health risks during practical applications. In addition, studies have found that some natural polysaccharides can inhibit the growth of ice crystals. Due to broad accessibility, regenerative properties, non-toxicity, and health benefits, these natural polysaccharides have received considerable attention in the field and are regarded as a potential candidate for the development of ideal food cryoprotectants.

Tamarind seed polysaccharide (TSP) is a galactoxyloglucan extracted and purified from the seed of *Tamarindus indica* L., and has desirable hydratability and thermal shock stability. According to the 2014 technical bulletin of Dsp Gokyo Company in Japan, TSP can stabilize the size of ice crystals in ice cream and is recommended as a stabilizer for frozen desserts. In view of the rising market of TSP in the domestic and foreign food fields, the applicant has conducted a comprehensive study on an ability of this polysaccharide to inhibit the growth of ice crystals. The ability of the TSP to inhibit ice crystal growth and recrystallization was found to be superior to some known frozen food stabilizers, such as carrageenan, guar gum, carboxymethylcellulose, and xanthan gum. However, the ice recrystallization inhibition activity of TSP is far inferior to that of natural antifreeze proteins and some synthetic polymers such as polyvinyl alcohol and other highly-active antifreezes. As a result, the TSP does not have the advantages of development and application simply as an ice recrystallization inhibitor. In addition, TSP has high viscosity and low dissolution efficiency, which are not conducive to applications of the TSP in low-viscosity food systems.

In the cutting-edge theory, an ability of ice-inhibiting molecules to participate in ice-water interaction and an appropriate size effect are two crucial factors of inhibiting ice crystal growth and recrystallization. Most natural polysaccharides with flexible structures tend to form dense self-aggregates through hydrogen bonds and hydrophobic interactions in a solution, resulting in a low degree of solvation for the molecular chains. Accordingly, these natural polysaccharides cannot form effective surface chemical properties to participate in ice-water interaction, nor can they form crowding and size effects that can effectively hinder the rapid growth of ice crystals at an ice-water interface. Therefore, all the known and reported natural polysaccharides exhibit a poor ice growth inhibition activity, and there is no highly active polysaccharide-based ice recrystallization inhibitor yet.

SUMMARY

The present disclosure provides a reconstructed TSP, and a preparation method and use thereof. Compared with natural TSP, the reconstructed TSP has lower viscosity and significantly improved ice recrystallization inhibition activity.

The present disclosure provides a reconstructed TSP, where the reconstructed TSP has a fibrous supramolecular structure with a length of greater than 300 nm.

The present disclosure further provides a preparation method of the reconstructed TSP, including the following steps:

- mixing a TSP aqueous solution with cellulase to allow cellulase enzymolysis to obtain a depolymerized TSP enzymolysis solution;
- allowing the depolymerized TSP enzymolysis solution to have enzyme deactivation, conducting solid-liquid separation, and subjecting an obtained supernatant to dialysis at a cut-off molar mass of 14 kg/mol to obtain a retentate;
- subjecting the retentate to freeze-drying to obtain a depolymerized TSP;
- redissolving the depolymerized TSP in water to obtain a depolymerized TSP aqueous solution; and
- mixing the depolymerized TSP aqueous solution with β-galactosidase to allow β-galactosidase enzymolysis to obtain a reconstructed TSP enzymolysis solution; where the reconstructed TSP enzymolysis solution includes the reconstructed TSP.

Preferably, the β-galactosidase is added at 1,500 U/L; and the β-galactosidase enzymolysis is conducted at 25° C. to 37° C. for 24 h to 48 h.

Preferably, after the β-galactosidase enzymolysis is completed, the preparation method further includes: subjecting the reconstructed TSP enzymolysis solution to a post-treatment; and

- the post-treatment includes: allowing the reconstructed TSP enzymolysis solution to have enzyme deactivation, and subjecting an obtained mixture to alcohol precipitation to obtain a precipitated product; and
- redissolving the precipitated product in water, and conducting freeze-drying to obtain the reconstructed TSP.

Preferably, the cellulase is added at 200 U/L; and the cellulase enzymolysis is conducted at a room temperature for 2 h to 4 h.

Preferably, the TSP aqueous solution has a concentration of 1 wt % to 3 wt % and a pH value of 5.0 to 5.5.

Preferably, the depolymerized TSP aqueous solution has a concentration of 1 wt % to 3 wt % and a pH value of 4.5 to 5.0.

The present disclosure further provides use of the reconstructed TSP or a reconstructed TSP prepared by the preparation method as an ice recrystallization inhibitor.

The present disclosure further provides an ice recrystallization inhibitor, including the reconstructed TSP or a reconstructed TSP prepared by the preparation method.

Beneficial Effects

The present disclosure provides a reconstructed TSP, where the reconstructed TSP has a fibrous supramolecular structure with a length of greater than 300 nm. In the present disclosure, cellulase depolymerizes TSP to a certain extent, reducing a solution viscosity of the polysaccharide. This mechanism unfolds dense self-aggregating coils of the natural TSP to form highly-solvated depolymerized long chains. About 40% of the strongly hydrophilic side-chain galactose on the depolymerized TSP is removed by β-galactosidase to adjust to an appropriate local hydrophilic-hydrophobic ratio, thereby driving assembly of depolymerized polysaccharide chains, thus forming a large-sized fibrous supramolecular structure. In this way, surface properties involved in ice crystal interactions and size effects that impede the rapid growth of ice crystals at the interface are significantly improved, such that an ice recrystallization inhibition activity is significantly improved compared with that of the natural TSP. The reconstructed TSP breaks through objective limitation of a weak activity of the natural TSP-based ice recrystallization inhibitors, and shows important theoretical and technical guiding significance for broadening use of polysaccharide for cryoprotection and developing highly-active polysaccharide-based ice recrystallization inhibitors.

Furthermore, in the present disclosure, the molecular remodeling of TSP is regulated by a two-step enzymatic method, so as to form a specific self-assembled solution structure. This method is simple, efficient, environmental-friendly, and low-cost. The prepared highly active polysaccharide-based ice recrystallization inhibitor has broad application prospects in the fields of biological and food cryoprotection.

BRIEF DESCRIPTION OF THE DRAWINGS

To describe the technical solutions in the examples of the present disclosure or in the prior art more clearly, the accompanying drawings required for the examples will be briefly described below.

DETAILED DESCRIPTION OF THE EMBODIMENTS

Figure 1:
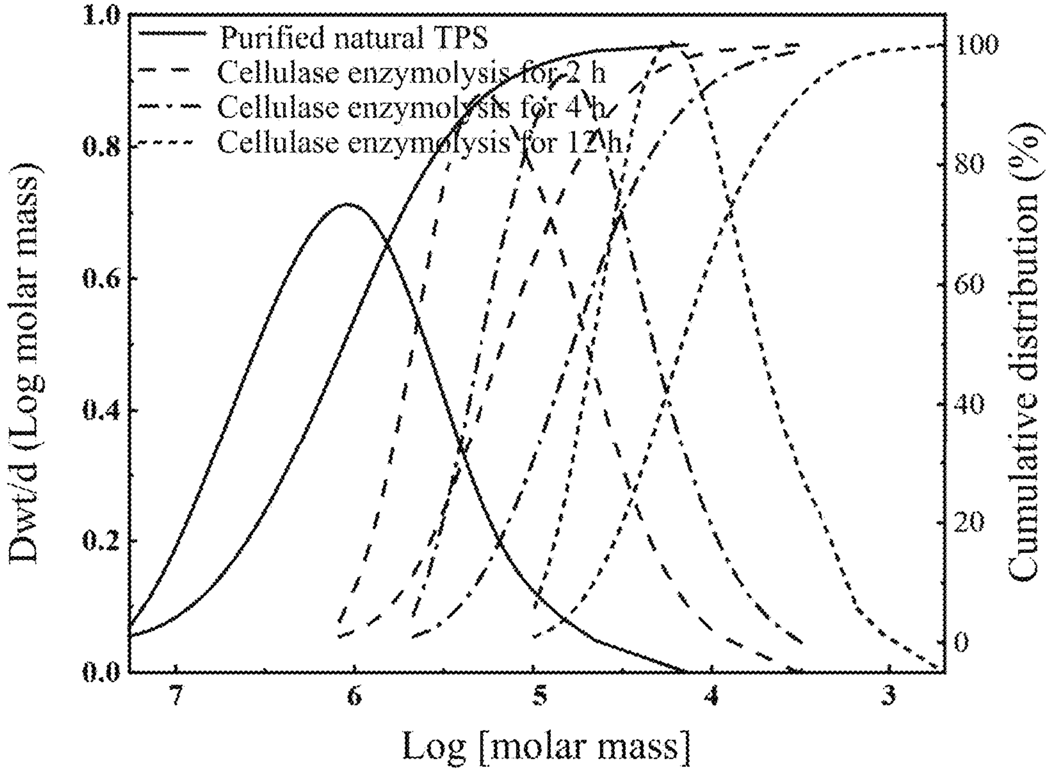
FIG. 1 shows molar mass distribution of a natural TSP and a depolymerized TSP with different cellulase treatment times in Example 1.

The present disclosure provides a reconstructed TSP, where the reconstructed TSP has a fibrous supramolecular structure with a length of greater than 300 nm.

The present disclosure further provides a preparation method of the reconstructed TSP, including the following steps:

- mixing a TSP aqueous solution with cellulase to allow cellulase enzymolysis to obtain a depolymerized TSP enzymolysis solution;
- allowing the depolymerized TSP enzymolysis solution to have enzyme deactivation, conducting solid-liquid separation, and subjecting an obtained supernatant to dialysis at a cut-off molar mass of 14 kg/mol to obtain a retentate;
- subjecting the retentate to freeze-drying to obtain a depolymerized TSP;
- redissolving the depolymerized TSP in water to obtain a depolymerized TSP aqueous solution; and
- mixing the depolymerized TSP aqueous solution with β-galactosidase to allow β-galactosidase enzymolysis to obtain a reconstructed TSP enzymolysis solution; where the reconstructed TSP enzymolysis solution includes the reconstructed TSP.

In the present disclosure, a purified TSP is preferably prepared, and the purified TSP is preferably obtained by precipitating a TSP with ethanol, specifically preferably including: mixing the TSP with an ethanol solution for precipitation, redissolving an obtained precipitate in water, and freeze-drying to obtain the purified TSP. The ethanol solution has a volume percentage of preferably 75% to 80%, more preferably 75%. The mixing for precipitation is conducted for preferably 12 h to 24 h. more preferably 24 h. There is no special limitation on operations of the redissolving and the freeze-drying, and conventional redissolving and freeze-drying steps in the art can be used. There is no special limitation on a source of the TSP, and conventional commercially available TSP in the field can be used. The purified TSP has a weight-average molar mass of preferably greater than 1.000 kg/mol, more preferably 1.000 kg/mol to 2.500 kg/mol.

In the present disclosure, preferably, the purified TSP is mixed with water and dissolved under stirring to obtain an TSP aqueous solution. The dissolving is conducted at preferably 70° C. to 90° C. more preferably 80° C. There is no special limitation on a dissolving time, as long as the purified TSP is completely dissolved. There is no special limitation on a specific operation of the stirring, and conventional stirring conditions in the art can be used. The TSP aqueous solution has a concentration of preferably 1 wt % to 3 wt %, more preferably 1 wt %.

In the present disclosure, a pH value of the TSP aqueous solution is preferably adjusted to 5.0 to 5.5, more preferably 5.5 with a sodium acetate buffer. The sodium acetate buffer has a concentration of preferably 1.0 M. and a pH value of preferably 5.0 to 5.5, more preferably 5.5.

In the present disclosure, a TSP aqueous solution after pH adjustment is mixed with cellulase to allow cellulase enzymolysis to obtain a depolymerized TSP enzymolysis solution. The cellulase is added at preferably 200 U/L. The cellulase enzymolysis is conducted at preferably a room temperature for preferably 2 h to 4 h. more preferably 4 h.

In the present disclosure, the depolymerized TSP enzymolysis solution is sequentially subjected to enzyme deactivation and solid-liquid separation to obtain a supernatant. The enzyme deactivation includes preferably boiling the depolymerized TSP enzymolysis solution for preferably 10 min. Preferably, the solid-liquid separation is conducted by centrifugation; there is no special limitation on a method and parameters of the solid-liquid separation, and conventional solid-liquid separation methods in the art can be used.

In the present disclosure, the supernatant is dialyzed at a cut-off molar mass of 14 kg/mol to obtain a retentate. Preferably, a dialysis bag is used for the dialysis, and specifically, the dialysis bag is preferably placed in deionized water for the dialysis. The dialysis is conducted for preferably 24 h to 72 h, more preferably 72 h. The dialysis can remove salts and low-molar-mass oligosaccharides in the supernatant.

In the present disclosure, the retentate is subjected to freeze-drying to obtain a depolymerized TSP. There is no special limitation on parameters of the freeze-drying, and conventional freeze-drying steps in the art can be used.

In the present disclosure, the depolymerized TSP has a weight-average molar mass of preferably 90 kg/mol to 201 kg/mol, more preferably 90 kg/mol.

In the present disclosure, the depolymerized TSP is redissolved in water to obtain a depolymerized TSP aqueous solution. The depolymerized TSP aqueous solution has a concentration of preferably 1 wt % to 3 wt %, more preferably 1 wt %.

In the present disclosure, a pH value of the depolymerized TSP aqueous solution is preferably adjusted to 4.5 to 5.0, more preferably 4.5 with a sodium acetate buffer. The sodium acetate buffer has a concentration of preferably 1.0 M, and a pH value of preferably 4.5 to 5.0, more preferably 4.5.

In the present disclosure, the depolymerized TSP aqueous solution after adjusting the pH value is mixed with β-galactosidase to conduct β-galactosidase enzymolysis to obtain a reconstructed TSP enzymolysis solution. The β-galactosidase is added at preferably 1,500 U/L. The β-galactosidase enzymolysis is conducted at preferably 25° C. to 37° C., more preferably 37° C. for preferably 24 h to 48 h, more preferably 48 h.

In the present disclosure, the method further includes preferably post-treatment; and the post-treatment includes: allowing the reconstructed TSP enzymolysis solution to have enzyme deactivation, and subjecting an obtained mixture to alcohol precipitation to obtain a precipitated product. The enzyme deactivation is preferably the same as that in the above technical solutions, and will not be repeated here.

In the present disclosure, the alcohol precipitation includes preferably; mixing the mixture with ethanol to allow precipitation to obtain a precipitated product. The mixture and the ethanol are at a volume ratio of preferably 1:(3-4), more preferably 1:3 or 1:4, and even more preferably 1:3.

In the present disclosure, the precipitated product is redissolved in water, and freeze-drying is conducted to obtain the reconstructed TSP. There is no special limitation on special parameters of the redissolving and the freeze-drying, and conventional redissolving and freeze-drying parameters in the art can be used.

In the present disclosure, TSP is used as a raw material, and a solution viscosity of the polysaccharide is reduced by cellulase depolymerization, such that self-aggregating spherical coils with a diameter of about 20 nm of TSP are unfolded to form highly solvated long chains. In this way, the hydration effect and surface reactivity of the polysaccharide molecular chain are effectively improved, thereby improving ice recrystallization inhibition activity. On this basis, about 40% of the strongly hydrophilic side-chain galactose on the depolymerized TSP is removed by β-galactosidase, and the local hydrophilic-hydrophobic ratio is adjusted to drive the assembly of polysaccharide chains to form large-sized fibrous supramolecules structure. This can significantly improve the surface properties and interface size effect involved in the ice crystal interaction, resulting in a dramatic increase in ice recrystallization inhibition activity compared to that of natural polysaccharides. Therefore, compared with the above-mentioned depolymerized TSP, the ice recrystallization inhibition activity has been further improved, breaking through an objective limitation of the weak activity of natural TSP-based ice recrystallization inhibitors.

Based on the above technical advantages, the present disclosure further provides use of the reconstructed TSP or a reconstructed TSP prepared by the preparation method as an ice recrystallization inhibitor.

The present disclosure further provides an ice recrystallization inhibitor, including the reconstructed TSP or a reconstructed TSP prepared by the preparation method.

In the present disclosure, a preparation method of the ice recrystallization inhibitor preferably includes: redissolving the reconstructed TSP in a solvent to obtain a reconstructed TSP solution, namely the ice recrystallization inhibitor. The solvent preferably includes, but is not limited to, water, PBS, or an aqueous solution containing salt ions. There is no special requirement on a concentration of the ice recrystallization inhibitor, and solutions prepared with the reconstructed TSP as an active ingredient all belong to the protection scope of the present disclosure.

In order to further illustrate the present disclosure, the technical solutions provided by the present disclosure will be described in detail below in conjunction with accompanying drawings and examples, but they should not be construed as limiting the protection scope of the present disclosure.

Example 1

A preparation method of a depolymerized TSP included the following steps:

1. A commercially available natural TSP was used as a raw material and precipitated with 75% ethanol aqueous solution for 24 h, an obtained precipitate was collected, redissolved, and freeze-dried to obtain a purified natural TSP. A molar mass of the purified natural TSP prepared in step 1 was determined by size exclusion chromatography, and the results were shown in FIG. 1.

As shown in FIG. 1: the purified natural TSP obtained in step 1 had a weight-average molar mass of about 2,412 kg/mol.

2. 10 g of the purified natural TSP prepared in step 1 was dispersed in 1 L of deionized water, stirred at 80° C. for 2 h to dissolve, to form a 1 wt % TSP aqueous solution; after adjusting a pH value of the TSP aqueous solution to 5.5 with a 1.0 M sodium acetate buffer at a pH value of 5.5, 200 U/L of cellulase (purchased from Sigma-Aldrich Co., Ltd.) was added, and enzymatically hydrolyzed at 25° C. for 2 h to obtain a depolymerized TSP enzymolysis solution; the depolymerized TSP enzymolysis solution was boiled to conduct enzyme deactivation for 10 min, cooled, centrifuged at 10,000 rpm for 10 min, and a supernatant was collected: the supernatant was dialyzed for 72 h to remove salt and low-molar-mass oligosaccharides using a regenerated cellulose dialysis bag with a cut-off molar mass of 14 kg/mol, and an obtained retentate was freeze-dried to obtain a depolymerized TSP.

A molar mass of the depolymerized TSP prepared in step 2 was determined by size exclusion chromatography, and the results were shown in the curve corresponding to 2 h of cellulase enzymolysis in FIG. 1.

As shown in FIG. 1, the depolymerized TSP obtained by hydrolysis with 200 U/L cellulase for 2 h in step 2 had a molar mass of about 201 kg/mol.

Test Example 1

Figure 2:
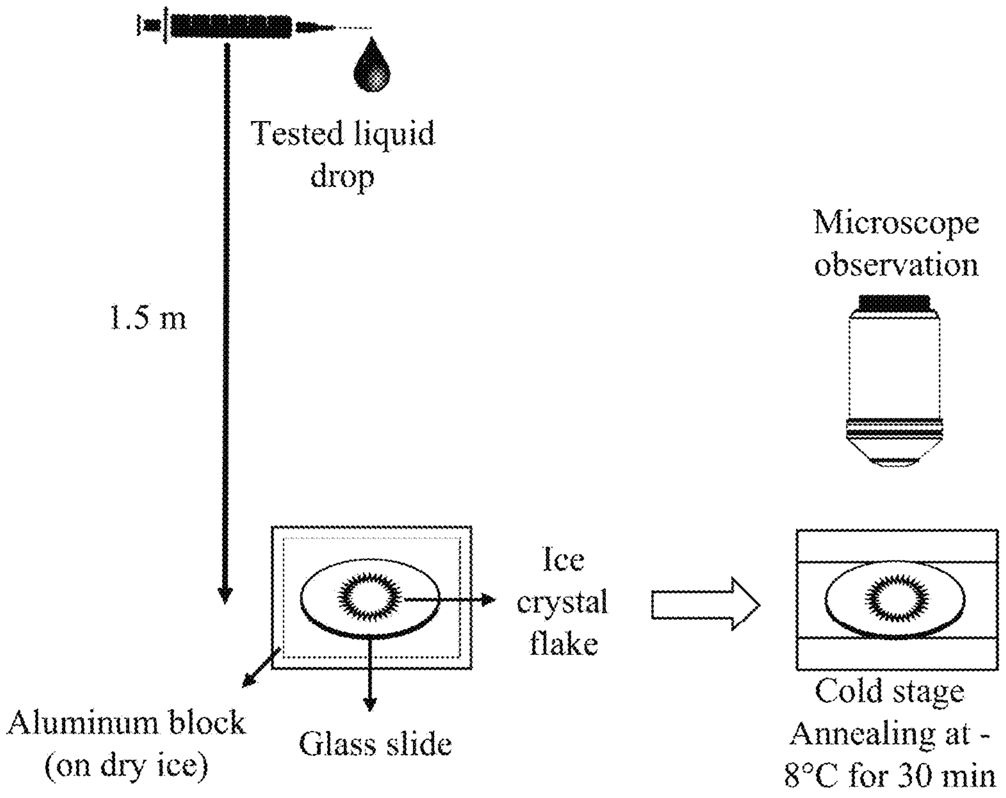
FIG. 2 shows a schematic diagram of an apparatus of an assay method of an ice recrystallization inhibition activity in Test Example 1.
Figure 3A:
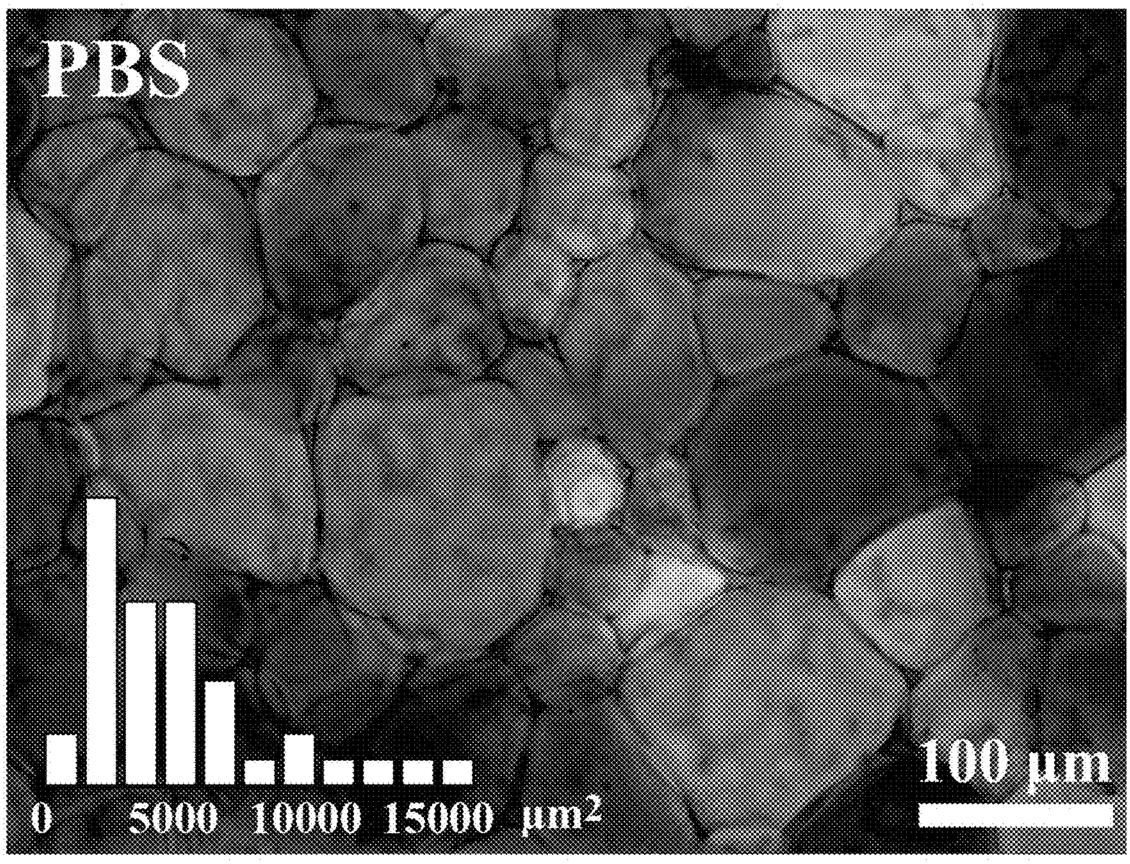
FIGS. 3A-3F show micrographs of natural TSP and a negative control polyethylene glycol (PEG) after ice crystal recrystallization in a PBS system for 30 min in Test Example 1.
Figure 3B:
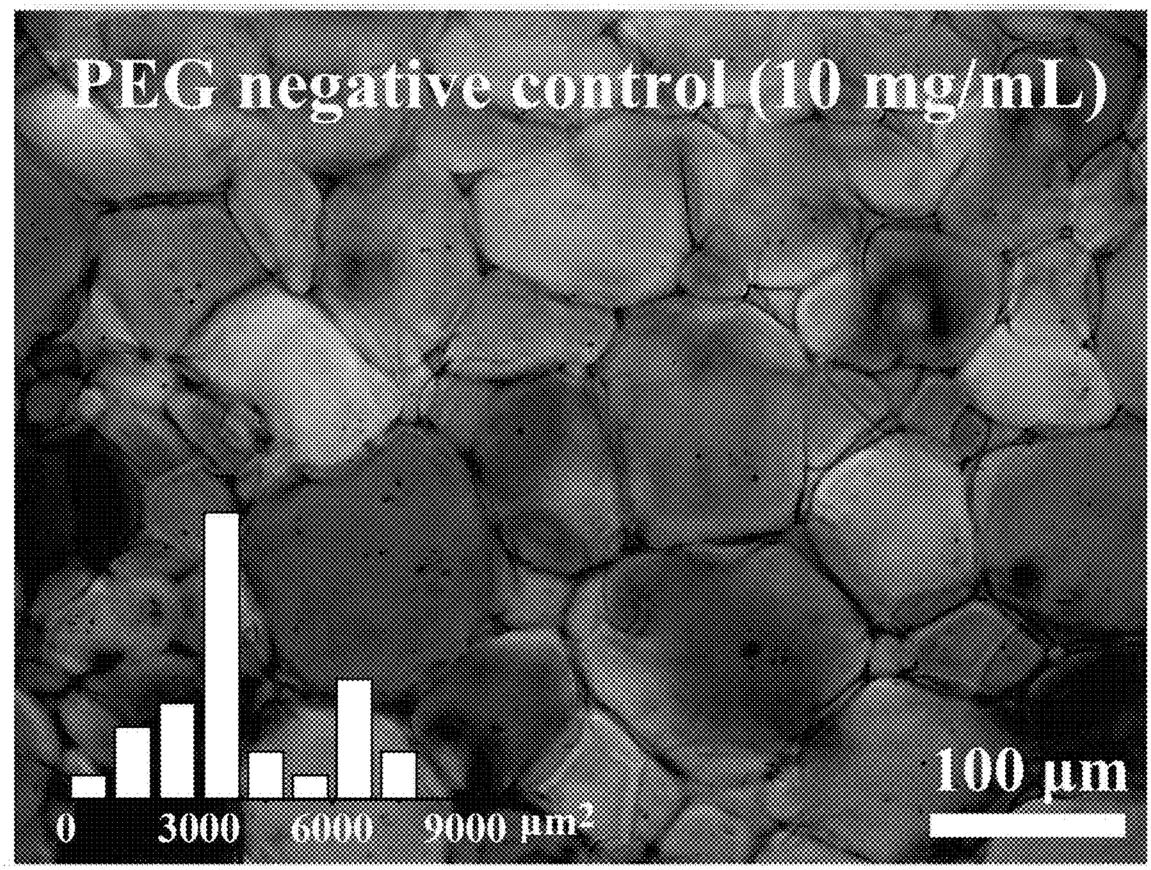
Figure 3C:
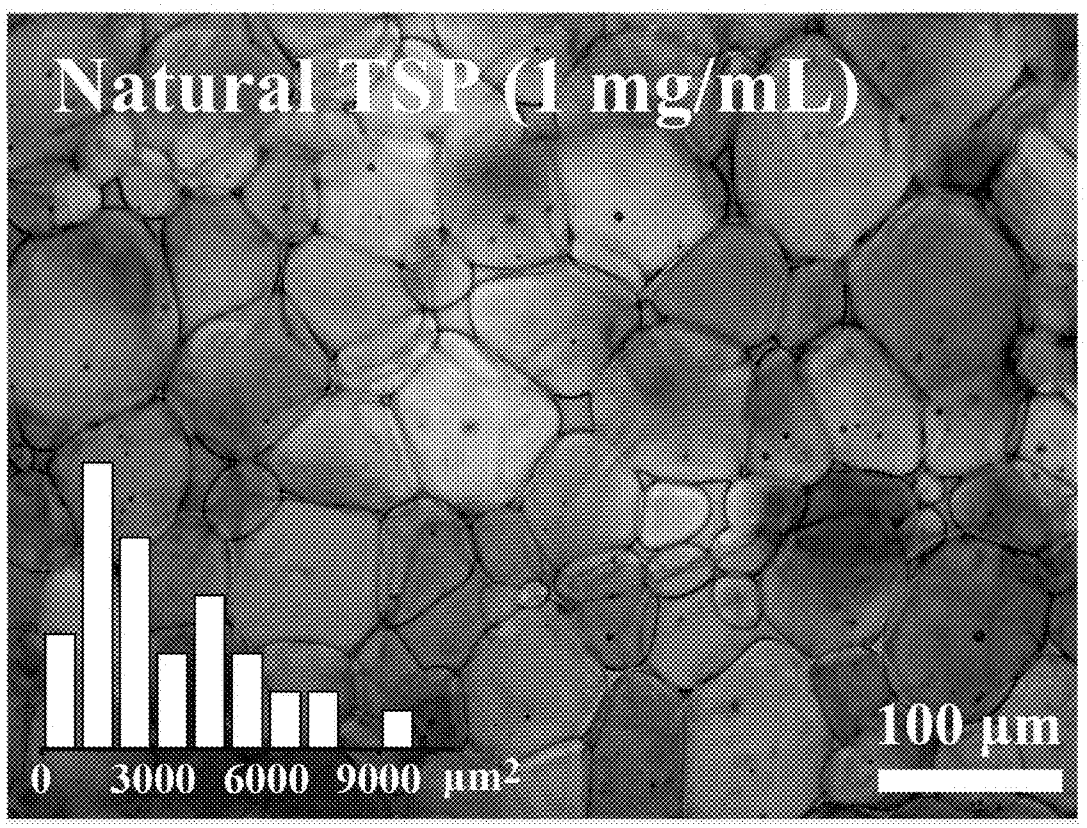
Figure 3D:
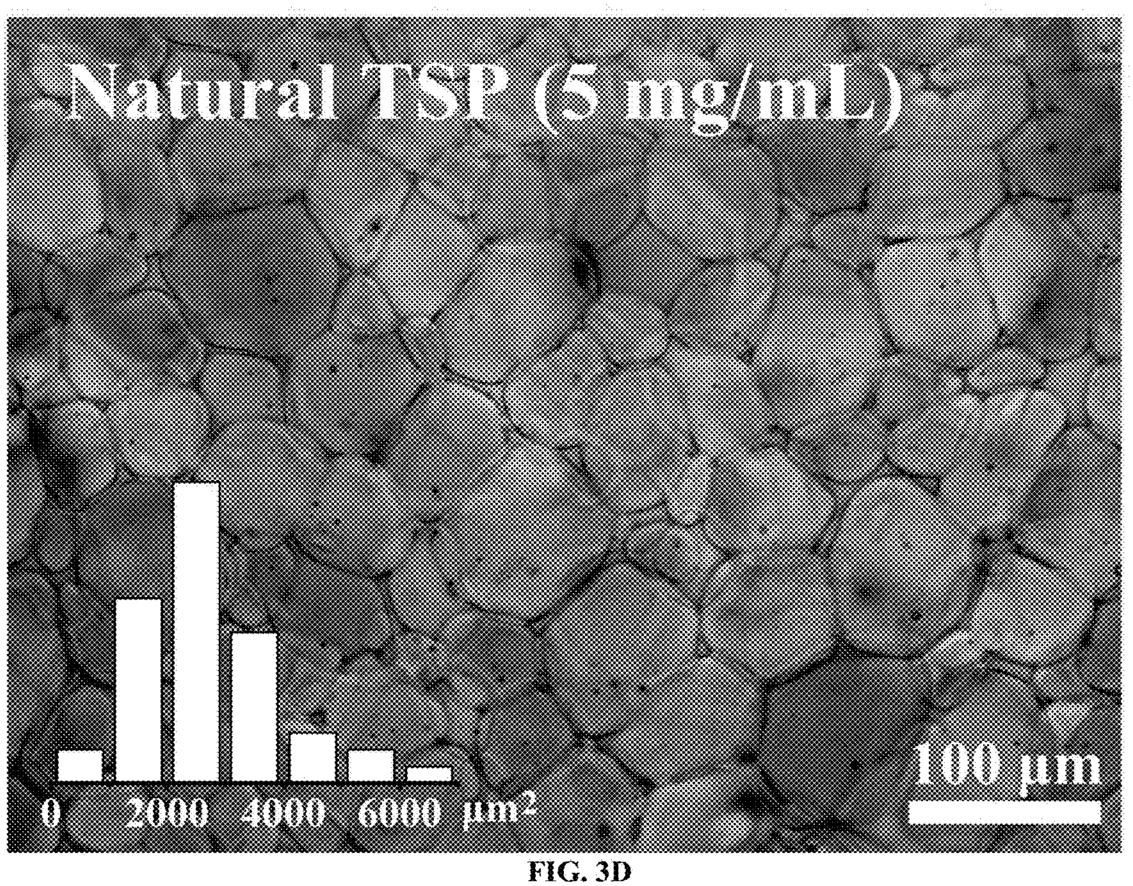
Figure 3E:
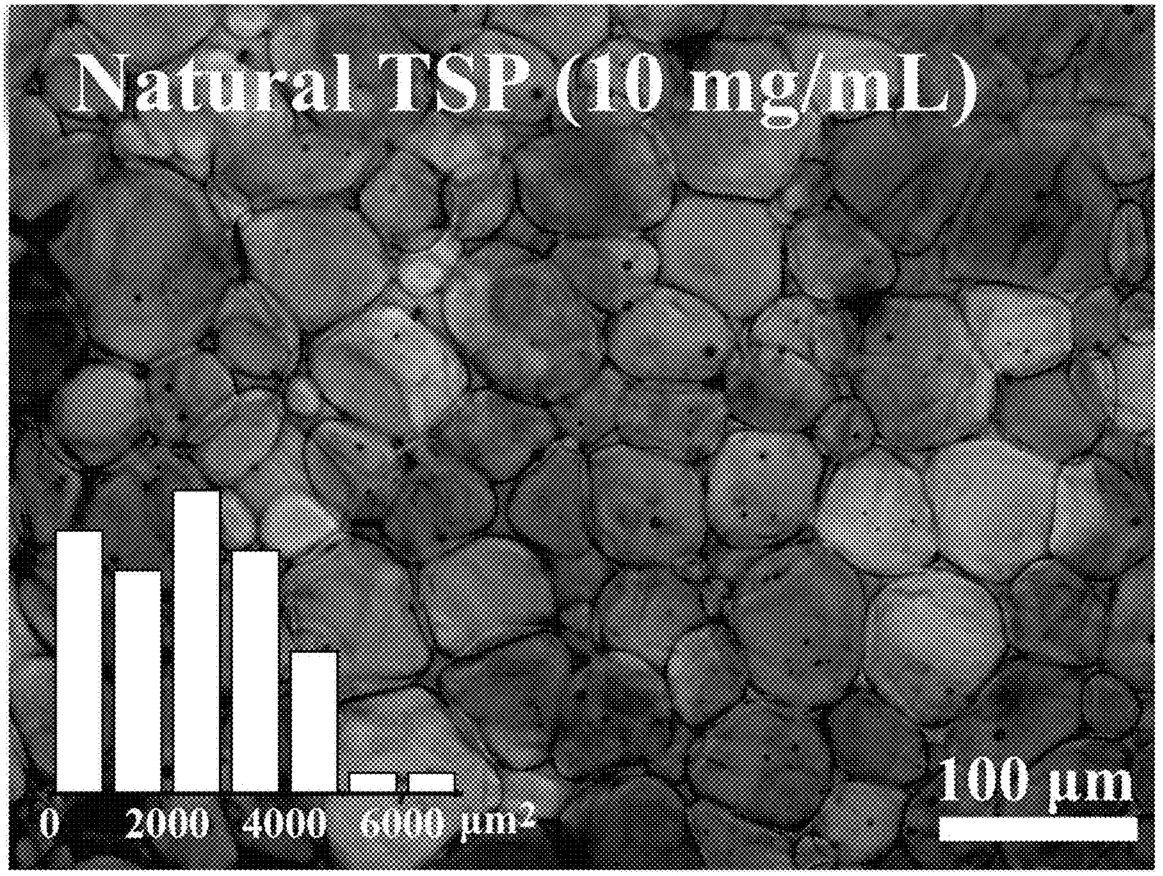
Figure 3F:
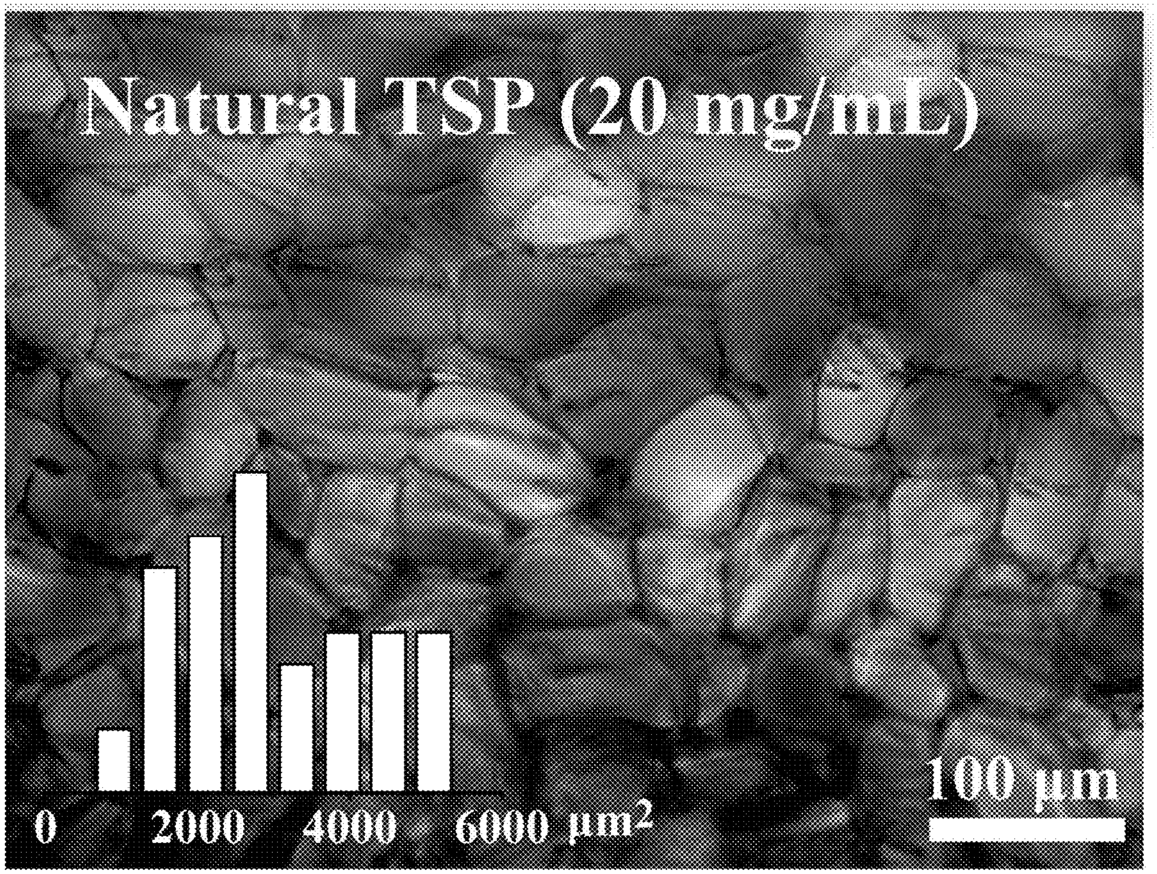
Figure 4A:
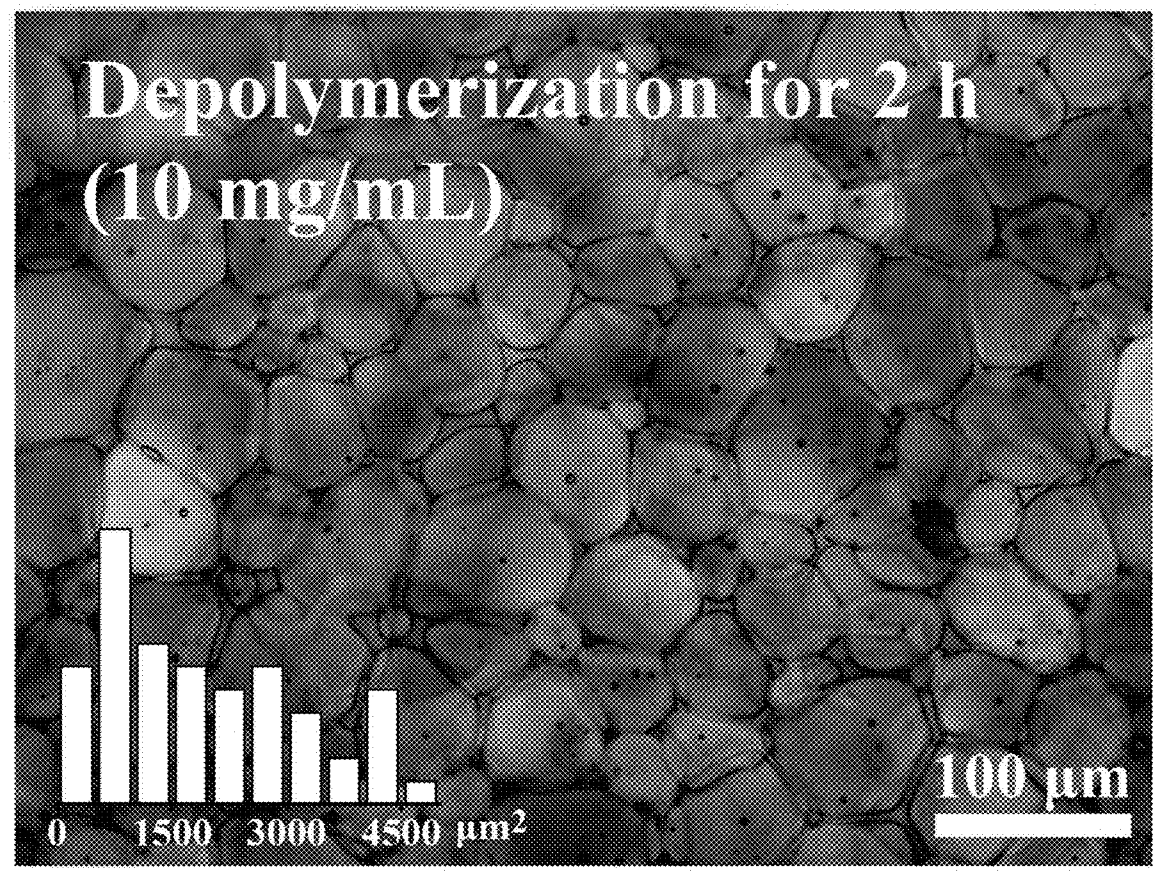
FIGS. 4A-4F show a micrograph of the depolymerized TSP after ice crystal recrystallization in the PBS system for 30 min in Test Example 1.
Figure 4B:
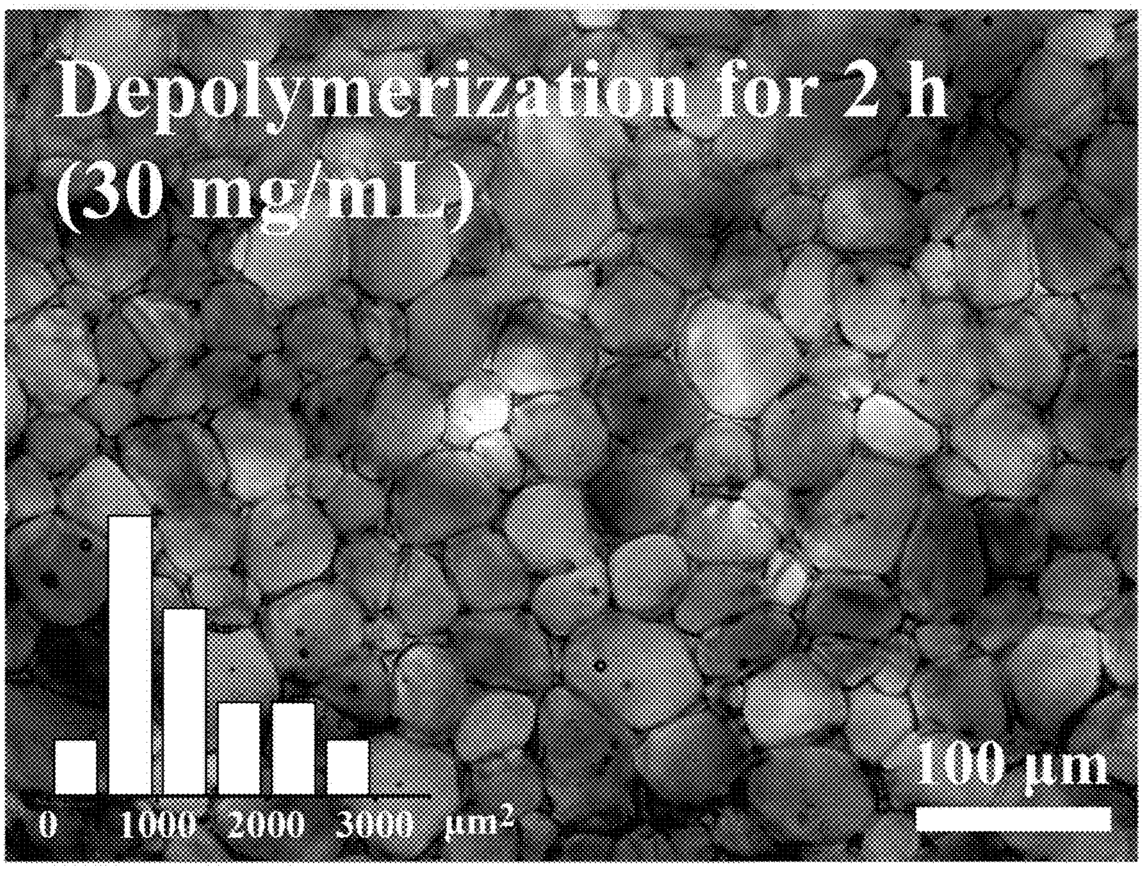
Figure 4C:
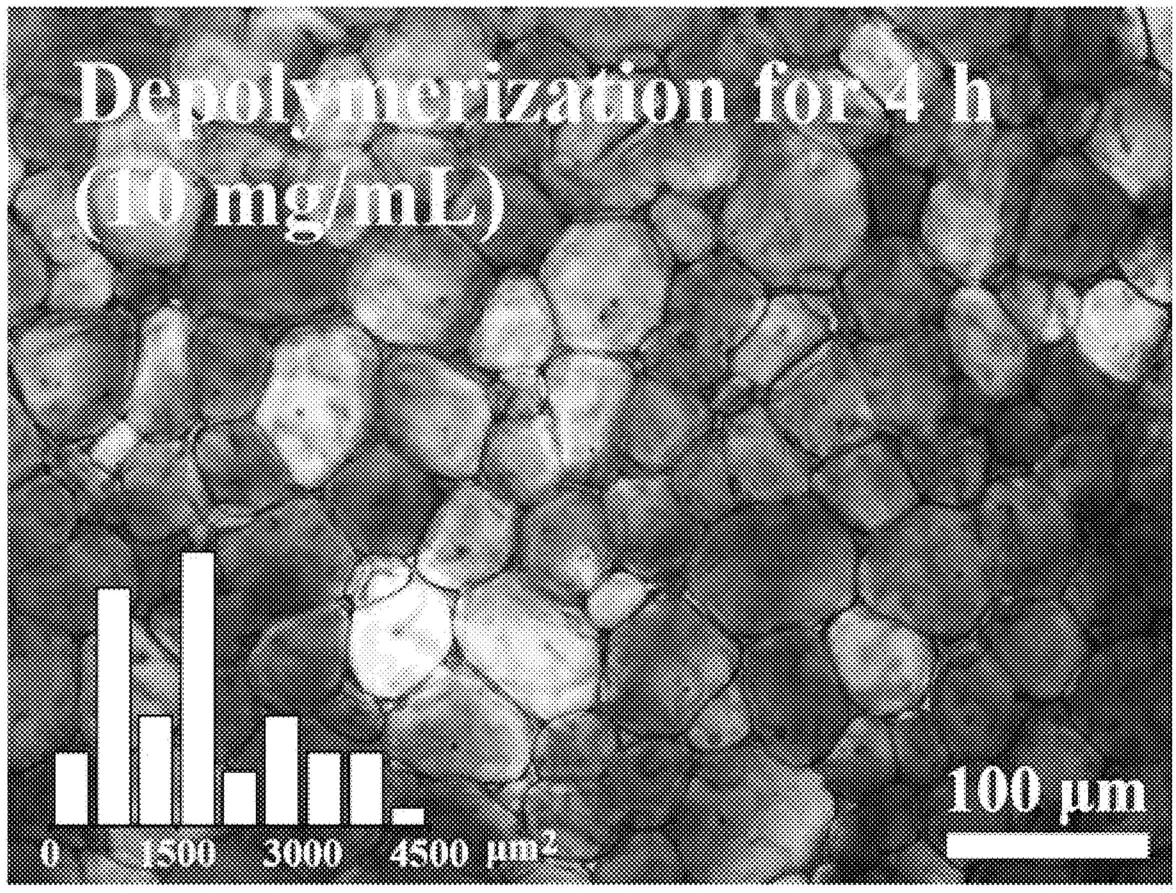
Figure 4D:
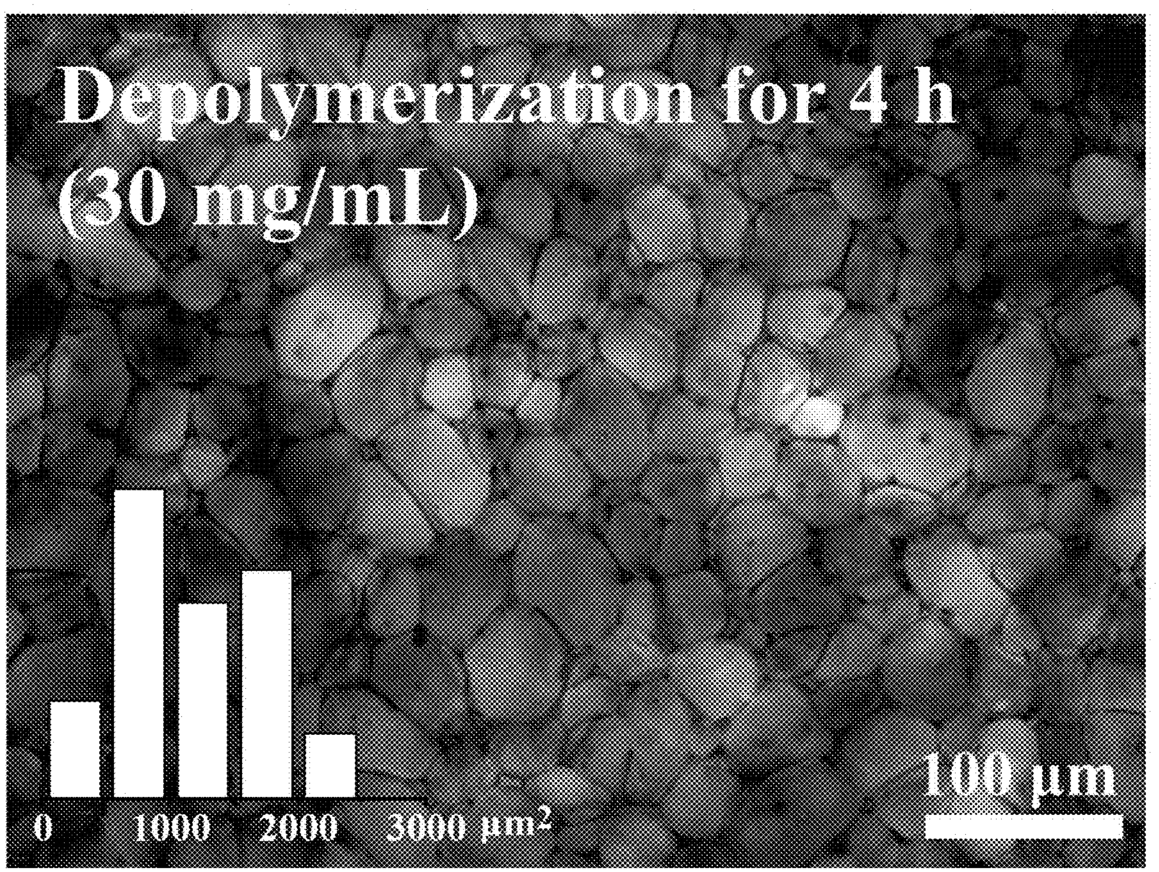
Figure 4E:
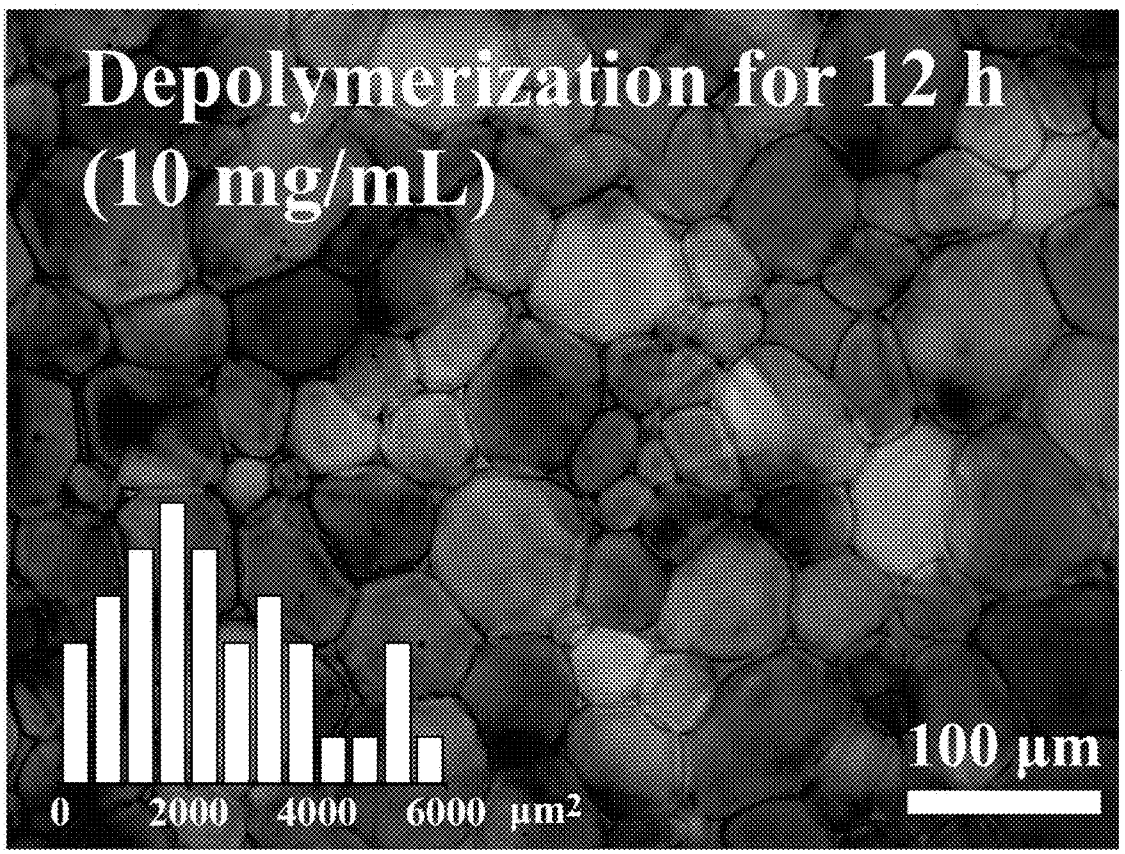
Figure 4F:
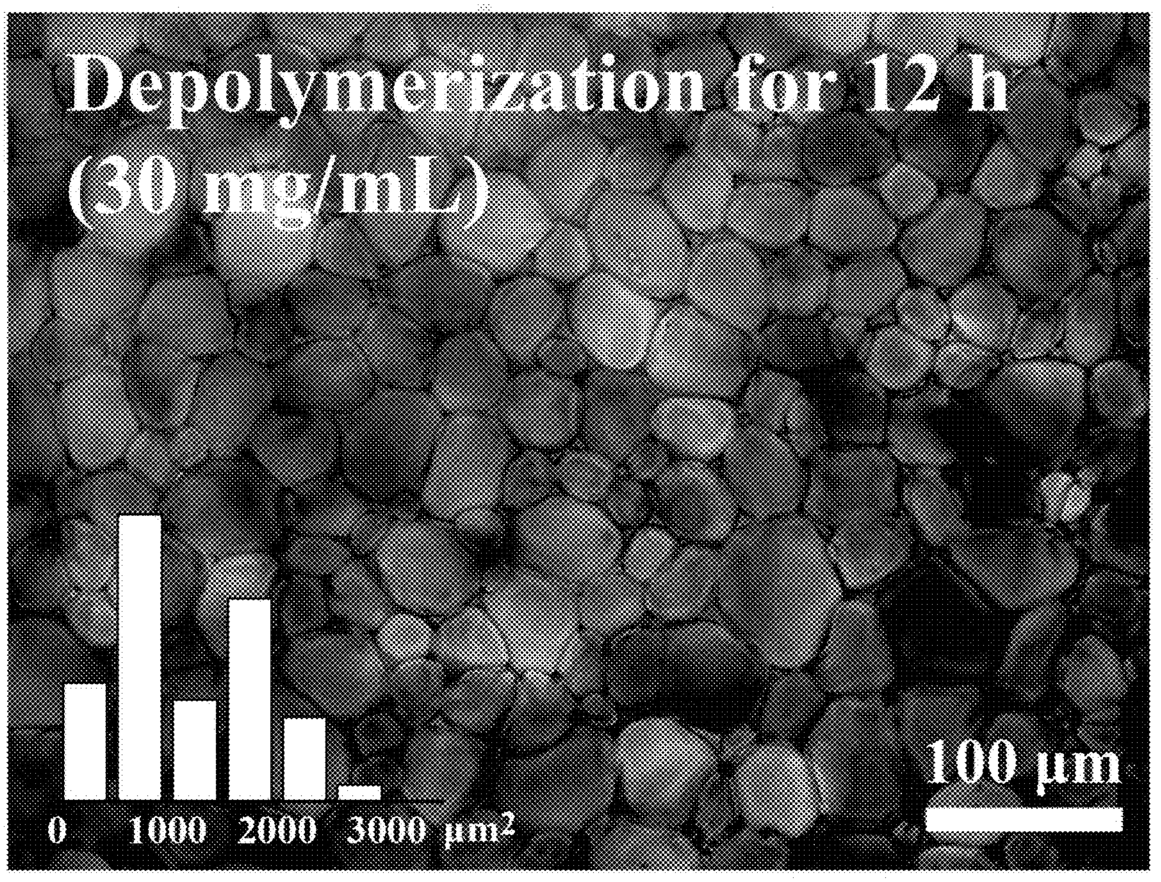
Figure 5:
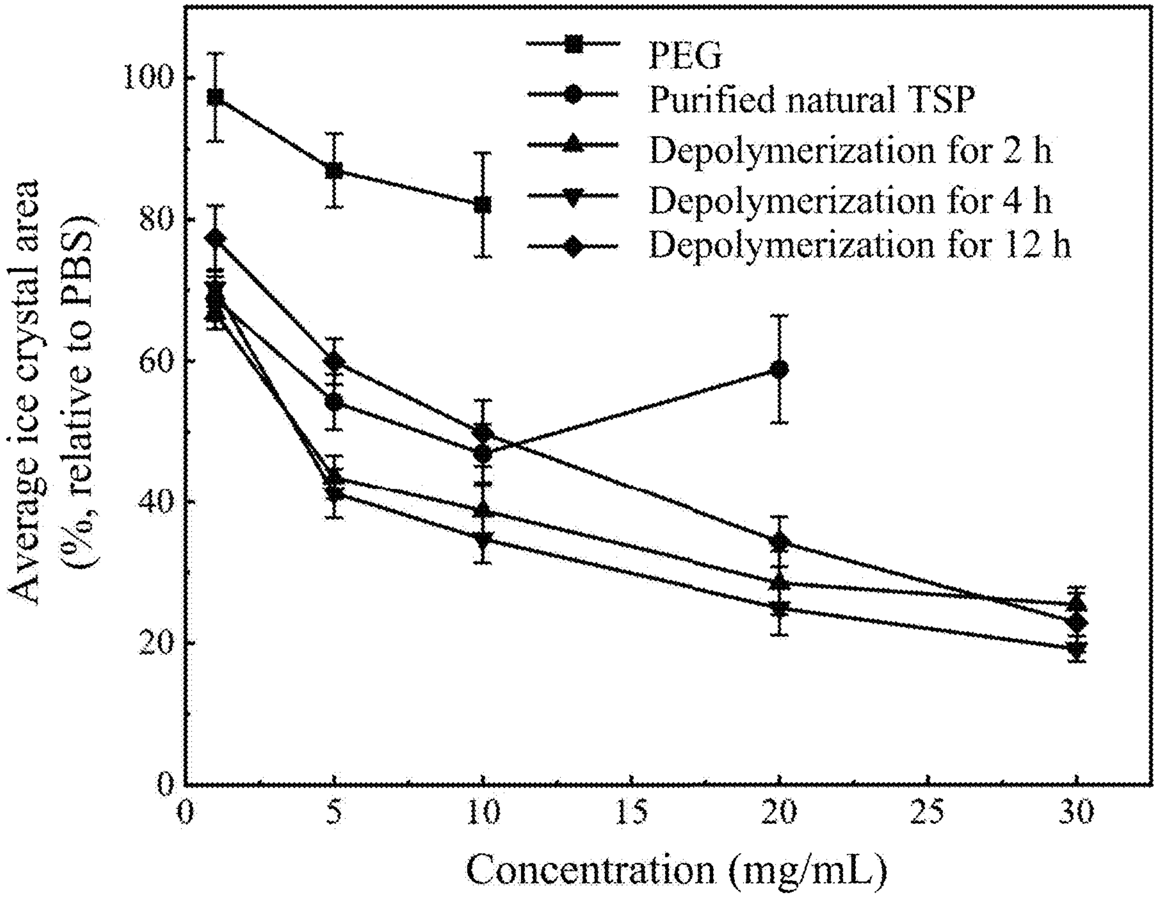
FIG. 5 shows statistical results of the ice recrystallization inhibition activity of the natural TSP and the depolymerized TSP in the PBS system in Test Example 1.

The ice recrystallization inhibition activity of TSP was determined using the "Splat cooling" test procedure shown in FIG. 2. The specific steps included: a sample was dissolved with 1×PBS buffer (containing 0.137 M NaCl), a salt concentration of the buffer could ensure a eutectic phase, avoiding false positives in the activity determination. 10 μL of the sample was collected with a microsyringe and added dropwise from a height of 1.5 m onto a @14 mm glass slide, which was placed on an aluminum metal block precooled with dry ice (−78° C.). The moment the liquid drop hit the glass slide, a thin layer of ice crystal flakes were formed on the glass slide. The glass slide was quickly transferred to a microscope equipped with a Linkam cryostage, and the ice crystal growth was observed at −8° C. for 30 min, photographed, and the number and area of ice crystals in the field of view were counted using ImageJ software.

The details of the sample were as follows:

The 1×PBS buffer (containing 0.137 M NaCl) was used as a solvent to dissolve the purified natural TSP prepared in step 1 and the depolymerized TSP prepared in step 2 to obtain a purified natural TSP at a concentration of (1-20) mg/mL solution and a depolymerized TSP solution at a concentration of (1-30) mg/mL. Using 1×PBS buffer as a blank control and polyethylene glycol (PEG) as a negative control, the purified natural TSP solution at (1-20) mg/mL and the depolymerized TSP solution at (1-30) mg/mL were tested by a "Splat cooling" test, the results were shown in FIGS. 3A-3F, FIGS. 4A-4F, and FIG. 5.

As shown in FIGS. 3A-3F, FIGS. 4A-4F, and FIG. 5: compared with natural TSP, the ice recrystallization inhibition activity of depolymerized TSP after 2 h of cellulase enzymolysis was significantly improved.

Example 2

The depolymerized TSP was prepared by the preparation method in Example 1, with the difference that the cellulase enzymolysis was conducted for 4 h.

Comparative Example 1

The depolymerized TSP was prepared by the preparation method in Example 1, with the difference that the cellulase enzymolysis was conducted for 12 h.

According to the size exclusion chromatography in Example 1, the molar mass distribution of the depolymerized TSP prepared in Example 2 and Comparative Example 1 was determined. The results were shown in the curves corresponding to cellulase enzymolysis for 4 h and cellulase enzymolysis for 12 h in FIG. 1. According to the "Splat cooling" test in Example 1, the ice recrystallization inhibition activity of the depolymerized TSP prepared in Example 2 and Comparative Example 1 was measured, and the results were shown in FIGS. 3A-3F, FIGS. 4A-4F, and FIG. 5.

As shown in FIG. 1, the molar masses of depolymerized TSP obtained by 200 U/L cellulase enzymolysis for 4 h and 12 h in step 2 were 90 kg/mol and 20 kg/mol, respectively.

As shown in FIGS. 3A-3F, FIGS. 4A-4F, and FIG. 5: the ice recrystallization inhibition activity of the depolymerized TSP obtained by enzymolysis for 4 h was slightly higher than that of the depolymerized TSP obtained by enzymolysis for 2 h. However, the ice recrystallization inhibition activity of depolymerized TSP obtained by enzymolysis for 12 h was not significantly improved compared with natural polysaccharides when the tested concentration was lower than 20 mg/mL.

Combining the molar mass distribution of depolymerized TSP and the antifreeze activity, the enzymolysis conditions with the maximum antifreeze activity were obtained: the cellulase was added at 200 U/L, and the enzymolysis time was 2 h to 4 h. The weight-average molar mass of depolymerized TSP under the enzymolysis conditions was 90 kg/mol to 201 kg/mol.

Example 3

Figure 6:
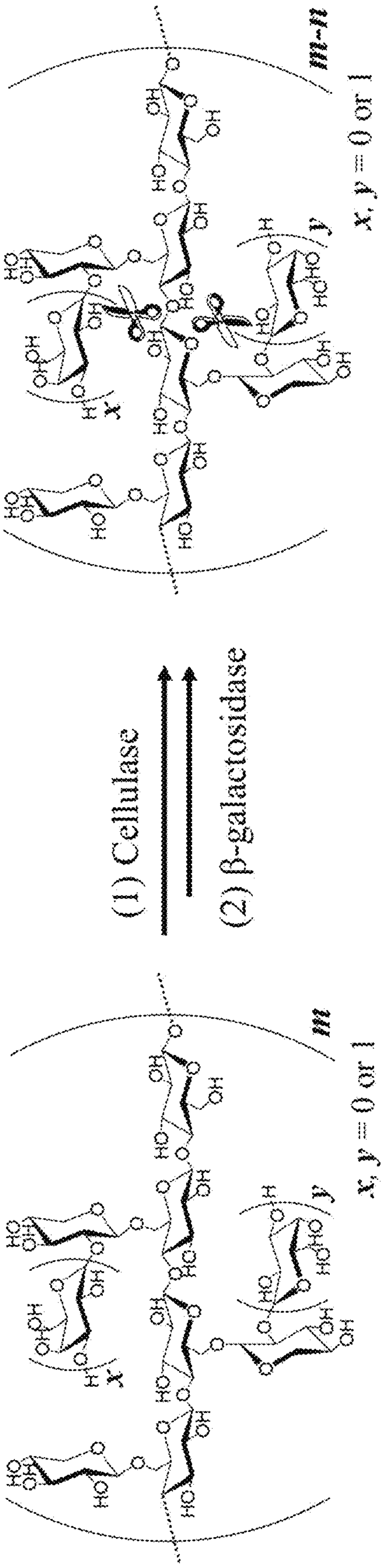
FIG. 6 shows a schematic structural diagram of molecular remodeling of the natural TSP induced by a two-step enzymatic method in Example 3.

A preparation method of a reconstructed TSP included the steps as follows, and a preparation process was shown in FIG. 6:

10 g of the depolymerized TSP obtained in Example 2 was added to 1 L of deionized water, stirred and dissolved to obtain a depolymerized TSP aqueous solution: a pH value of the depolymerized TSP aqueous solution was adjusted to 4.5 with a 1.0 M sodium acetate buffer at a pH value of 4.5, 1,500 U/L β-galactosidase (purchased from Sigma-Aldrich) was added, and a reaction was conducted by stirring at 37° C. for 24 h, boiled to conduct enzyme deactivation for 10 min; after cooling, 3 times a volume of ethanol was added for precipitation, a collected precipitated product was redissolved in 1 L of deionized water, and freeze-dried to obtain a depolymerized TSP from which galactose was partially removed.

Example 4

The reconstructed TSP was prepared by the preparation method in Example 3, with the difference that the β-galactosidase was conducted for 48 h.

Comparative Example 2

The reconstructed TSP was prepared by the preparation method in Example 3, with the difference that the β-galactosidase was conducted for 1 h.

Comparative Example 3

The reconstructed TSP was prepared by the preparation method in Example 3, with the difference that the β-galactosidase was conducted for 4 h.

Comparative Example 4

The reconstructed TSP was prepared by the preparation method in Example 3, with the difference that the β-galactosidase was conducted for 12 h.

Test Example 2

Figure 7:
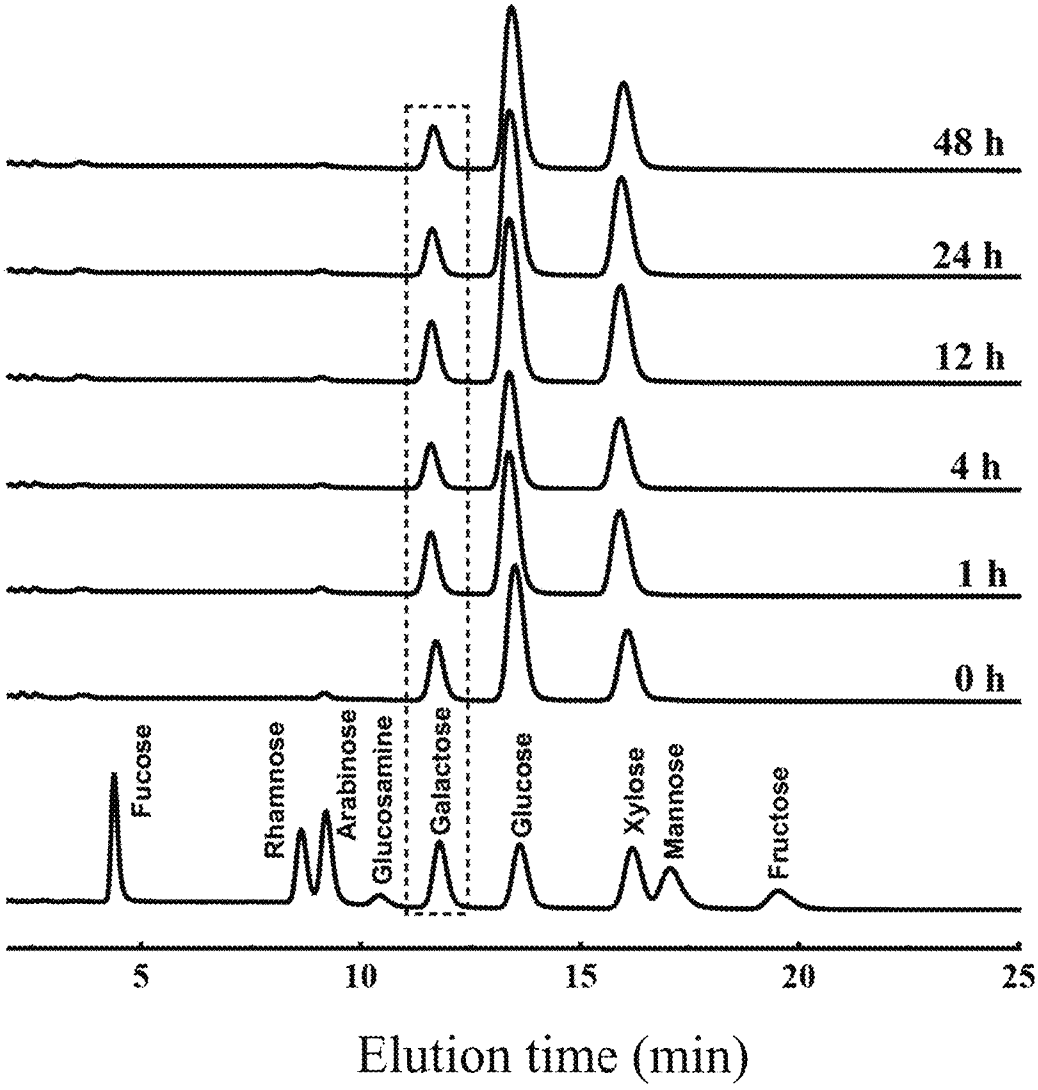
FIG. 7 shows changes in a monosaccharide composition of polysaccharides after the depolymerized TSP (prepared in Example 2) in Test Example 2 is treated with β-galactosidase for different periods of time.
Figure 8:
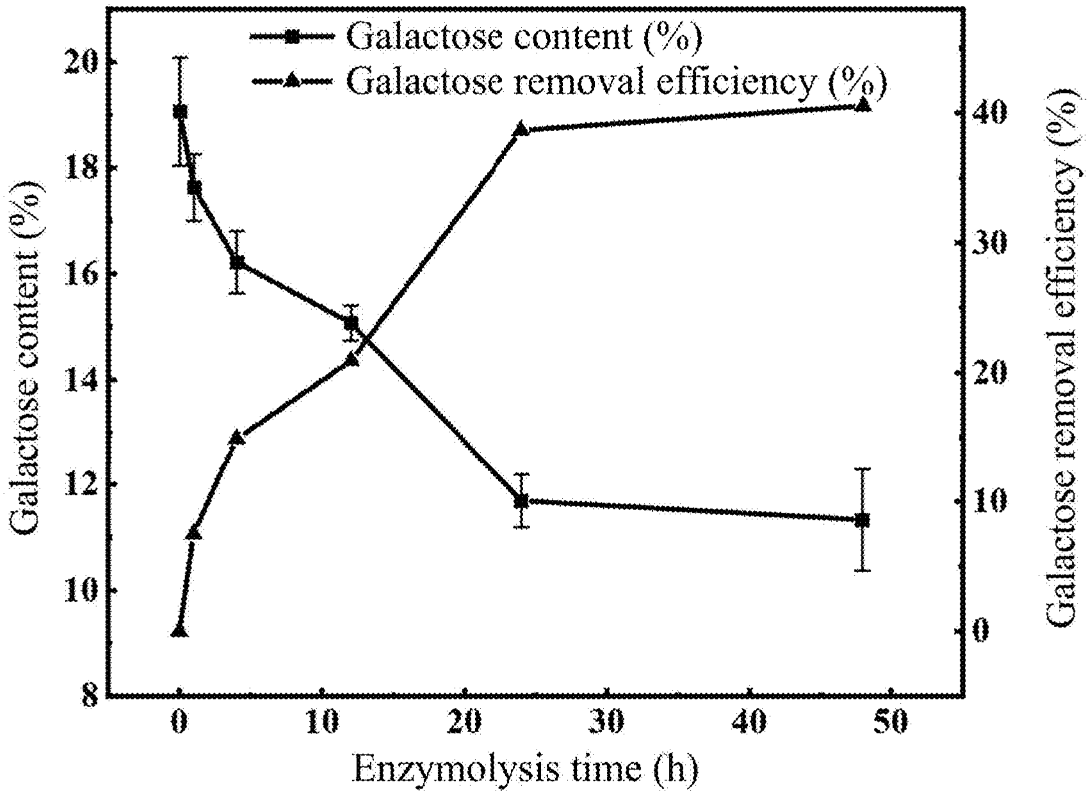
FIG. 8 shows changes in a side chain galactose content and a galactose removal efficiency of polysaccharides after the depolymerized TSP is hydrolyzed by β-galactosidase in Test Example 2.
Figure 9A:
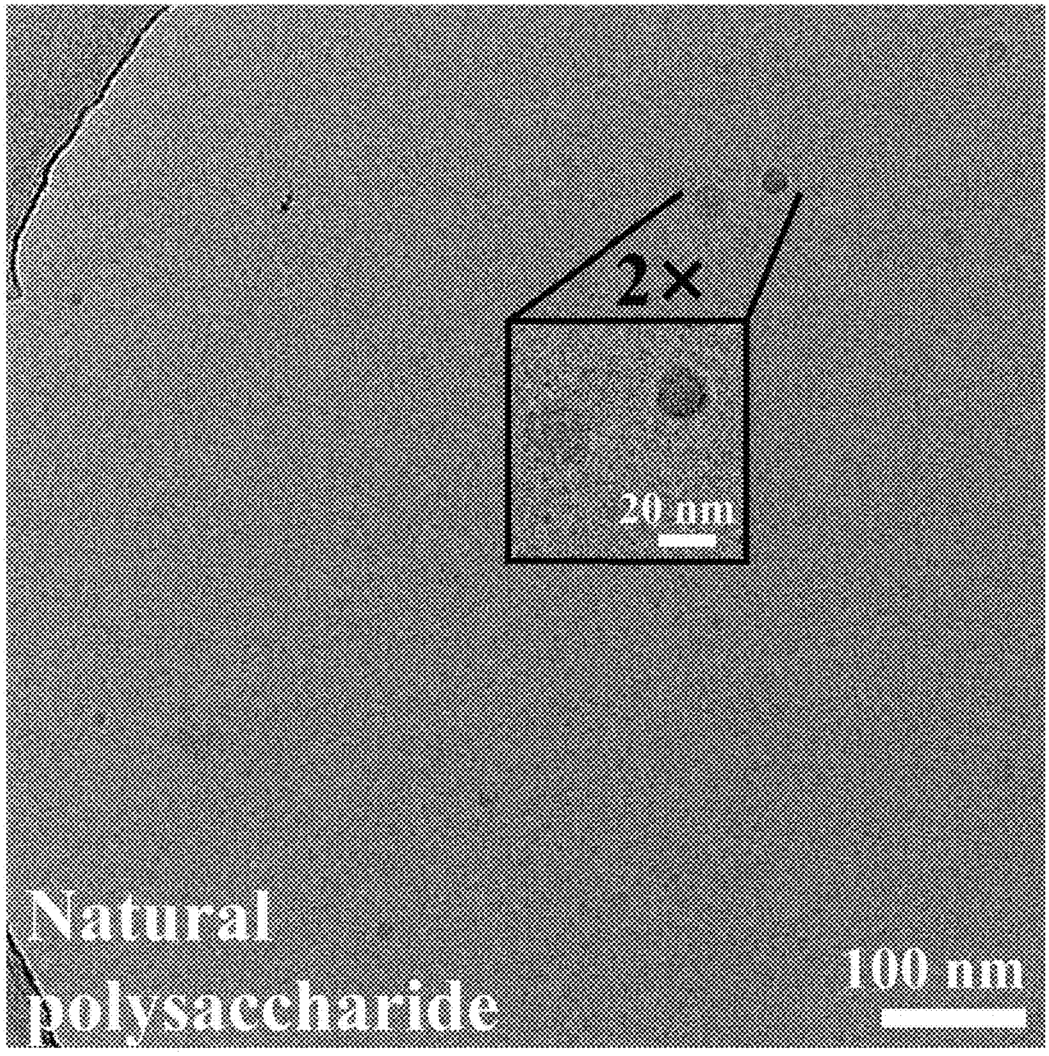
FIGS. 9A-9D show cryo-transmission electron microscopy (TEM) image of the natural TSP, the depolymerized TSP, and the reconstructed TSP in an aqueous solution in Test Example 3.
Figure 9B:
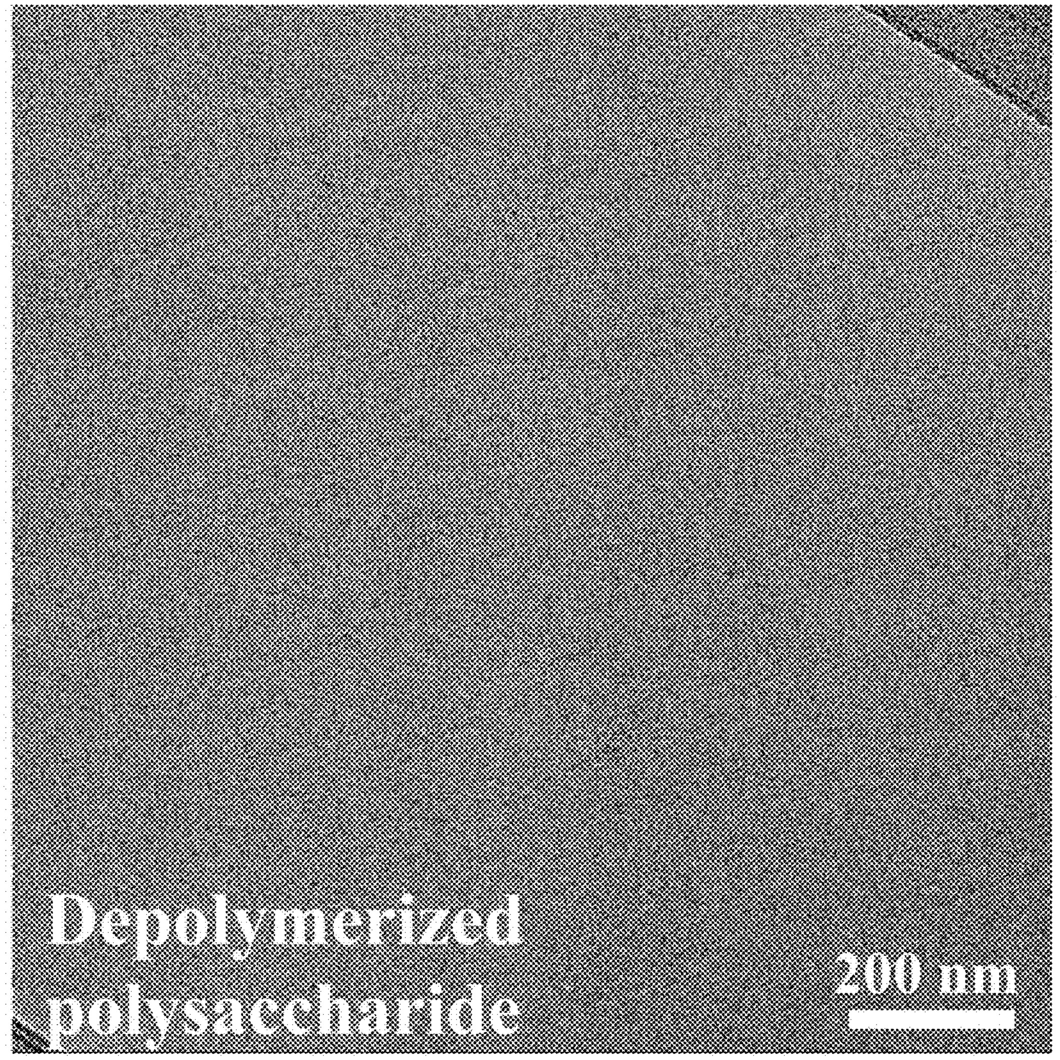
Figure 9C:
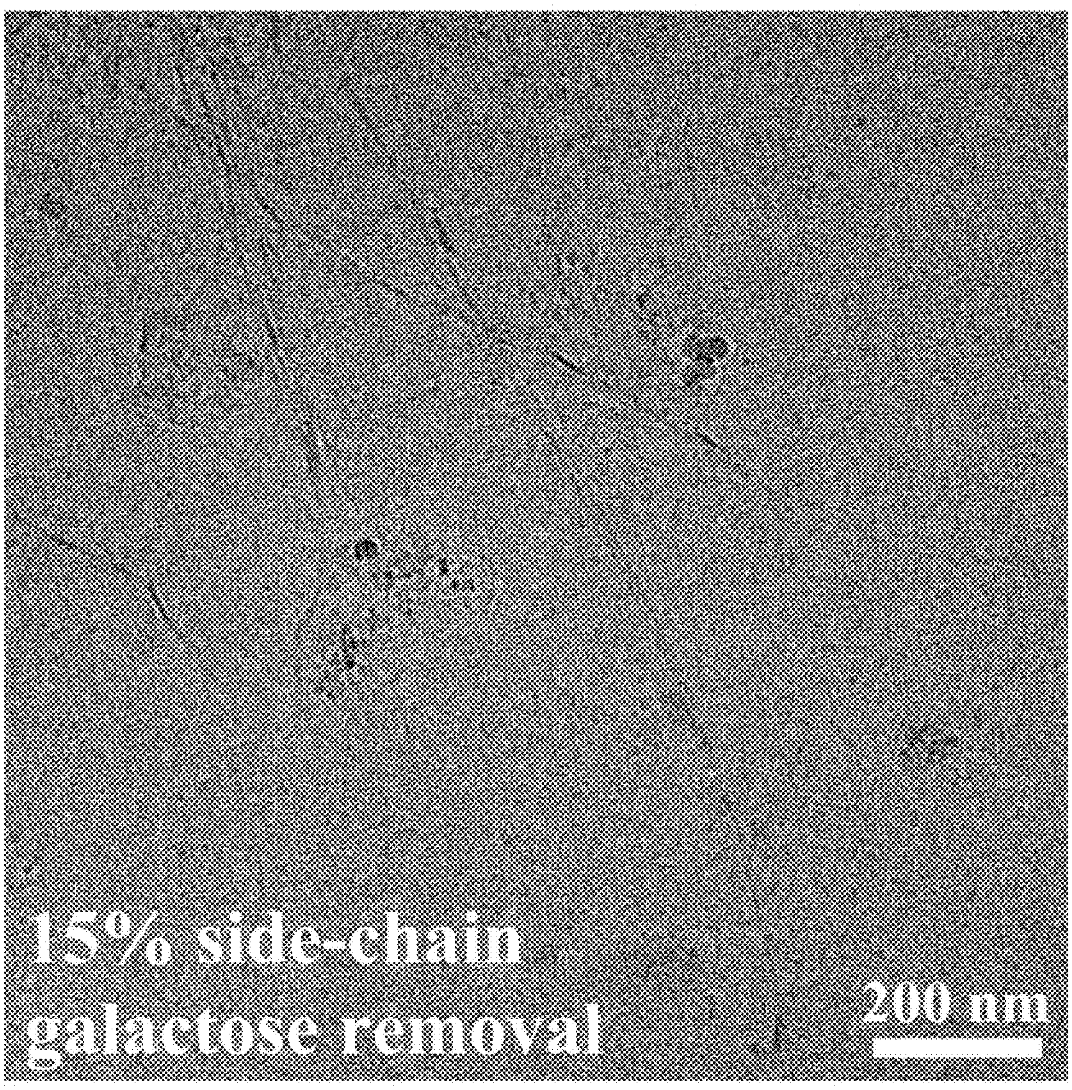
Figure 9D:
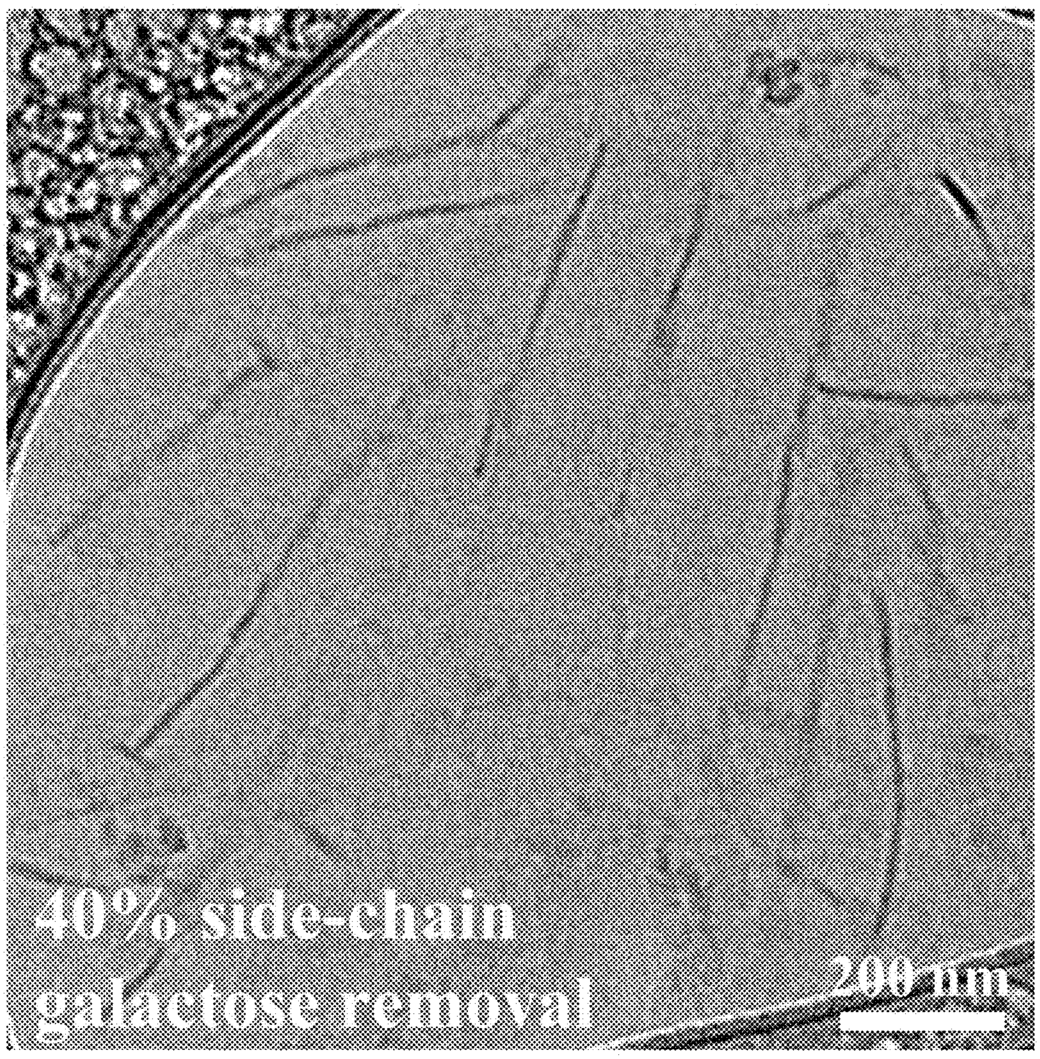

The depolymerized TSP prepared in Example 2 and the reconstructed TSP prepared in Examples 3 to 4 and Comparative Examples 2 to 4 were measured by high-performance liquid chromatography-pulsed amperometric detection (HPLC-PAD), and the results were shown in FIG. 7 and shown in FIG. 8.

As shown in FIG. 7 and FIG. 8: after the depolymerized TSP (at a weight-average molar mass of 90 kg/mol) was hydrolyzed by β-galactosidase, the removal efficiency of side-chain galactose gradually increased with time: the removal efficiency of galactose was 15% after 4 h of enzymolysis, and about 40% at 24 h and 48 h of enzymolysis. The galactose removal efficiency of the reconstructed TSP prepared in Examples 3 to 4 was about 40%; compared with the enzymolysis for 24 h in Example 3, the galactose content of the reconstructed TSP obtained by enzymolysis for 48 h in Example 4 did not further significantly decrease.

Test Example 3

The purified natural TSP prepared in Example 1, the depolymerized TSP prepared in Example 2, the reconstructed TSP prepared in Example 3, and the reconstructed TSP prepared in Comparative Example 3 were observed by cryo-transmission electron microscopy. Specifically, the natural TSP prepared in Example 1, the depolymerized TSP prepared in Example 2, the reconstructed TSP prepared in Example 3, and the reconstructed TSP prepared in Comparative Example 3 were dissolved in water to form a 10 mg/mL aqueous solution separately, and observed after vitrification. The results were shown in FIGS. 9A-9D. In FIGS. 9A-9D, natural polysaccharides represented purified natural TSP (scale bar=100 nm), depolymerized polysaccharides represented depolymerized TSP prepared in Example 2 (scale bar=200 nm), 40% side-chain galactose removal represented reconstructed TSP prepared in Example 3 (scale bar=200 nm), and 15% side-chain galactose removal represented the reconstructed TSP prepared in Comparative Example 3 (scale bar=200 nm).

As shown in FIGS. 9A-9D: in a 10 mg/mL aqueous solution, natural TSP mainly formed a spherical coil structure with a diameter of about 20 nm, and there was no obvious structured polysaccharide molecule in the cryo-transmission electron microscopy field of view after depolymerization. This indicated that the molecular chains of depolymerized TSP were well solvated and dispersed uniformly in the solution. The reconstructed polysaccharides with 15% side chain galactose removal formed a small amount of irregular fibrous structures and aggregates, while the reconstructed polysaccharide with 40% side chain galactose removed self-assembled in the solution to form a uniform fibrous supramolecular structure with a specific structure through intermolecular entanglement.

Test Example 4

Figure 10:
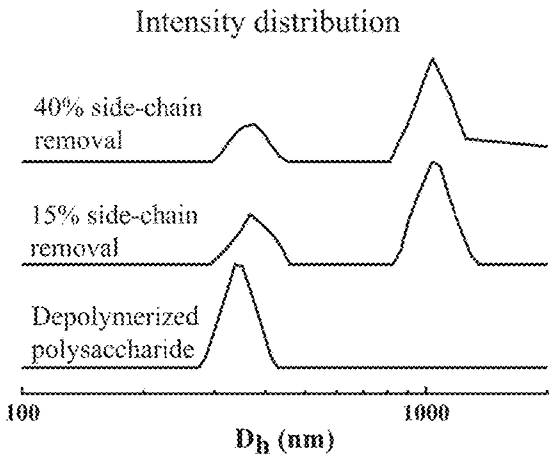
FIG. 10 shows particle size distribution of the depolymerized TSP and the reconstructed TSP in Test Example 3.

The particle size distribution of the depolymerized TSP prepared in Example 2, the reconstructed TSP prepared in Example 3, and the depolymerized TSP prepared in Comparative Example 3 was further tested by dynamic light scattering, and the results were shown in FIG. 10. The depolymerized polysaccharide represented the depolymerized TSP prepared in Example 2, the 40% side-chain galactose removal represented the reconstructed TSP prepared in Example 3, and the 15% side-chain galactose removal represented the reconstructed TSP prepared in Comparative Example 3.

As shown in FIG. 10: the depolymerized TSP formed a uniform distribution in the solution, and its hydrodynamic diameter is 300 nm to 400 nm: the reconstructed TSP prepared by removing 15% side chain galactose only formed a small amount of large-sized self-assembly: the reconstructed TSP prepared by removing 40% of the side chain galactose formed a large number of evenly distributed supramolecular self-assemblies, and its number-average hydrodynamic diameter distribution was 800 nm to 1200 nm.

Test Example 4

Figure 11:
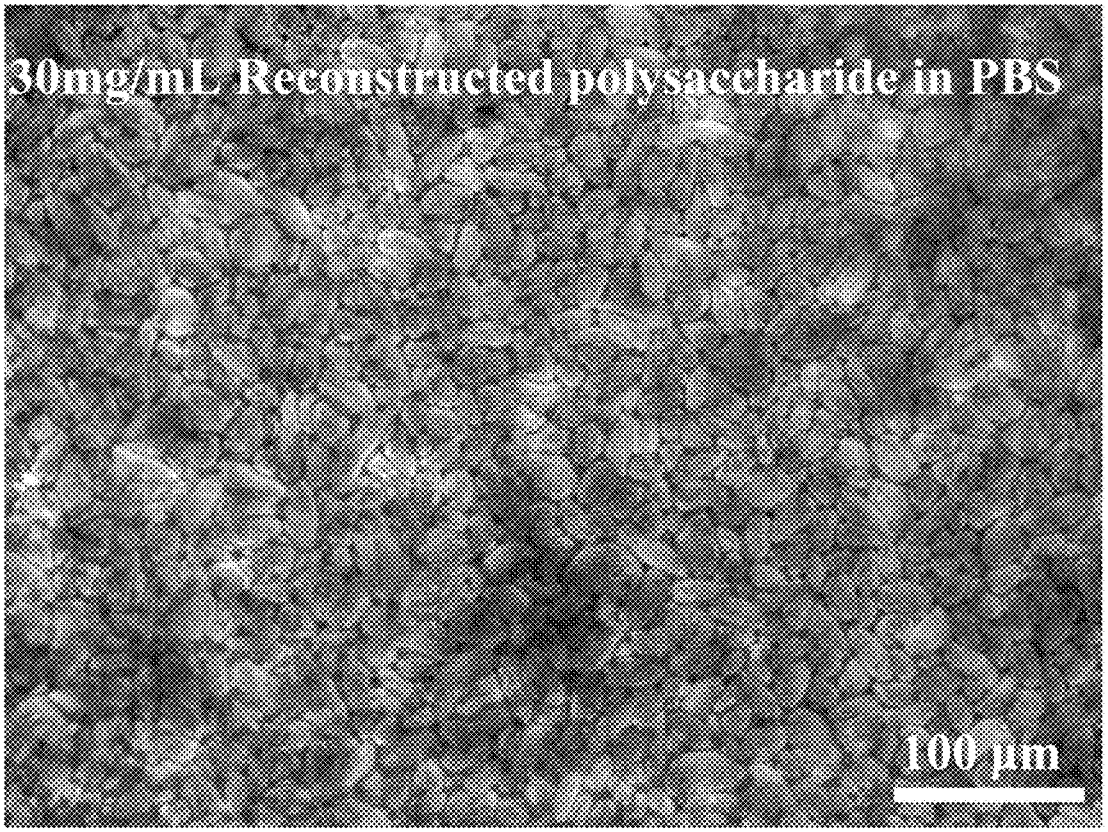
FIG. 11 shows an ice crystal micrograph of the reconstructed TSP in the PBS system after 30 min of ice crystal recrystallization in Test example 4.

The ice recrystallization inhibition activity of the reconstructed TSP prepared in Example 3 was measured by the method in Test Example 1, and the results were shown in FIG. 11. With polyethylene glycol (PEG) as a negative control, the area of ice crystal particles formed by the depolymerized TSP prepared in Example 2, the reconstructed TSP prepared in Example 3, and the reconstructed TSP prepared in Comparative Example 3 relative to PBS buffer at different concentrations was measured, and compared with the blank control group, the results were shown in FIG. 12. Depolymerized polysaccharide represented the depolymerized TSP prepared in Example 2, 40% side-chain removal represented the reconstructed TSP prepared in Example 3, and 15% side-chain removal represented the reconstructed TSP prepared in Comparative Example 3.

Figure 12:
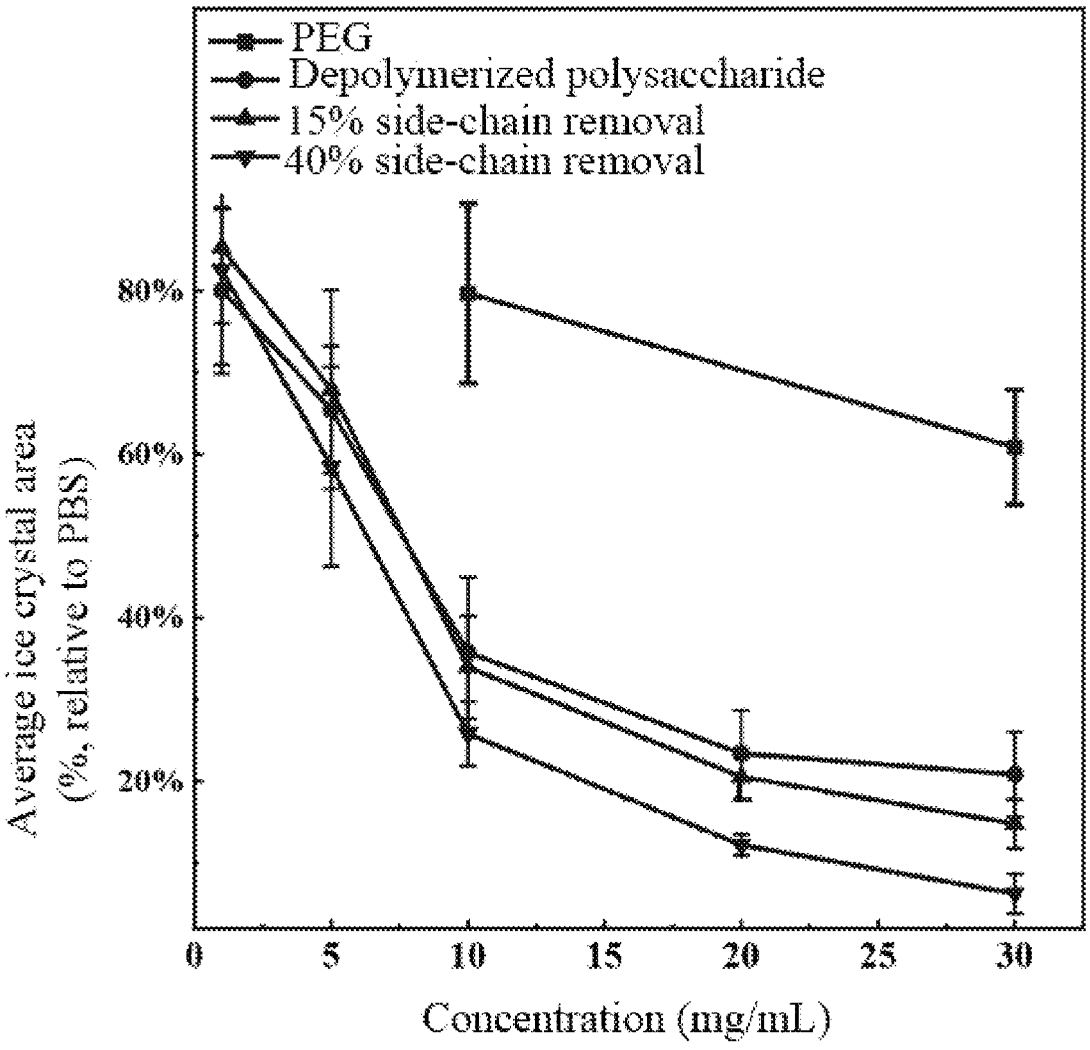
FIG. 12 shows statistical results of the ice recrystallization inhibition activity of the PEG negative control, the depolymerized TSP, and the reconstructed TSP in the PBS system in Test Example 4.
Figure 13A:
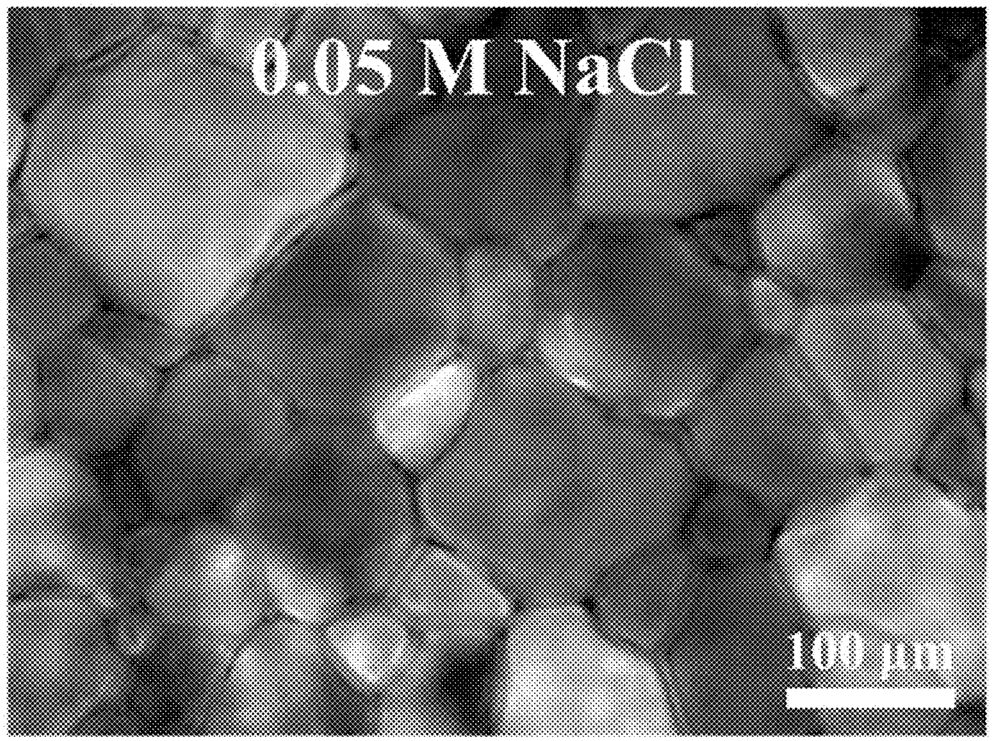
FIGS. 13A-13D show micrographs of ice crystals of the depolymerized TSP and the reconstructed TSP in a 0.05 M NaCl system after 30 min of ice crystal recrystallization in Test Example 5.
Figure 13B:
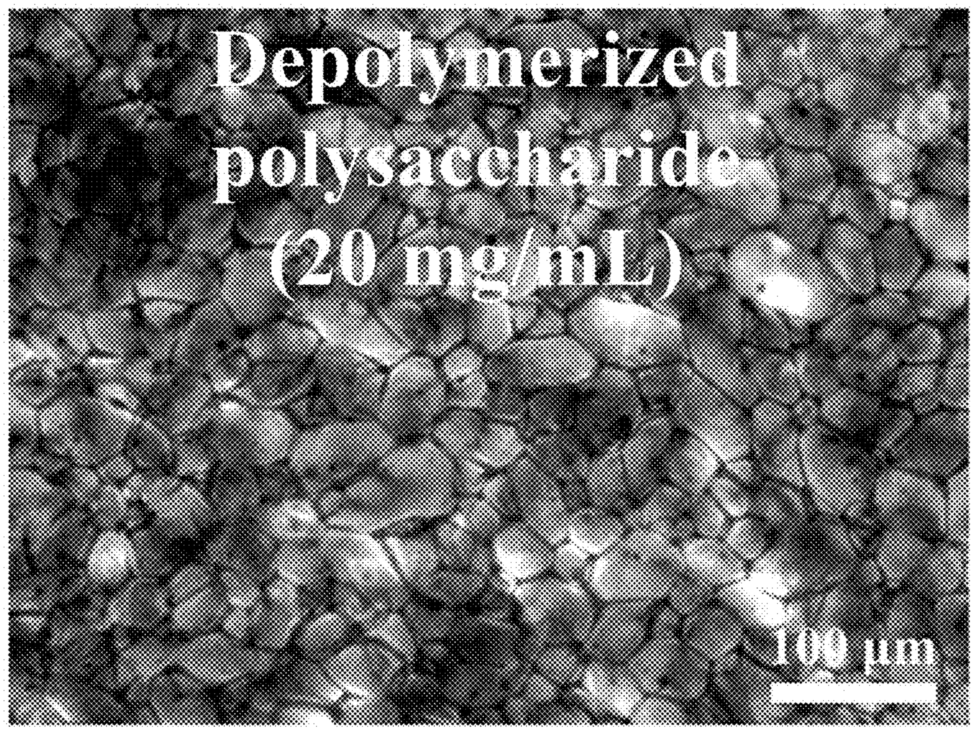
Figure 13C:
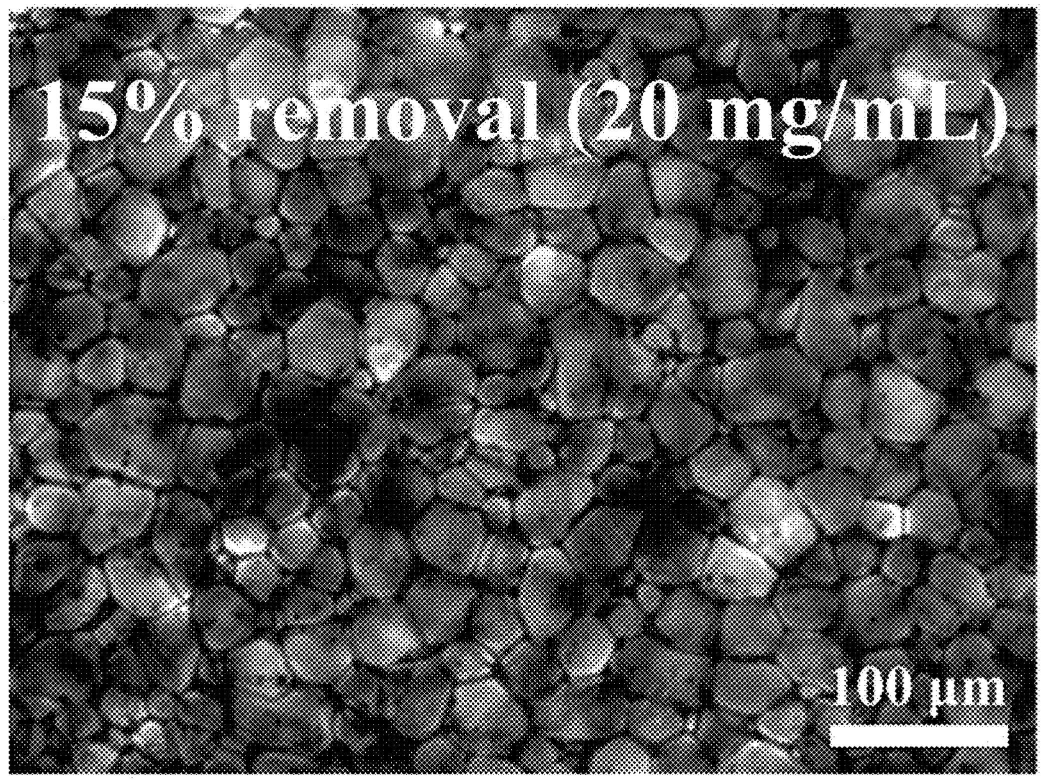
Figure 13D:
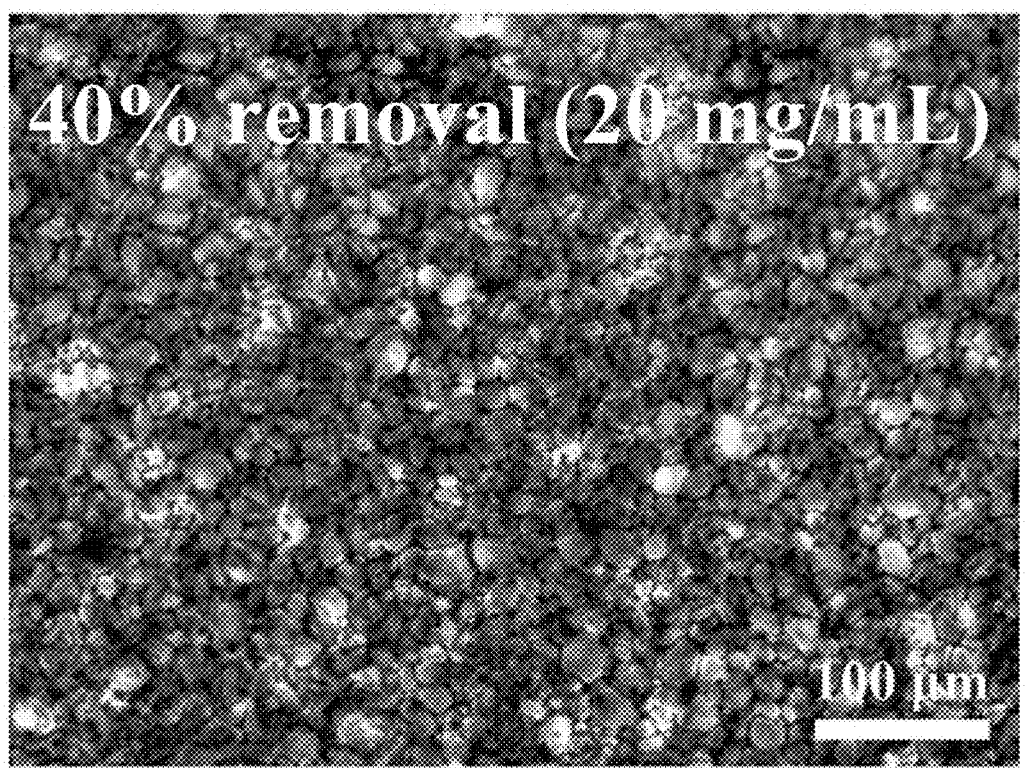
Figure 14:
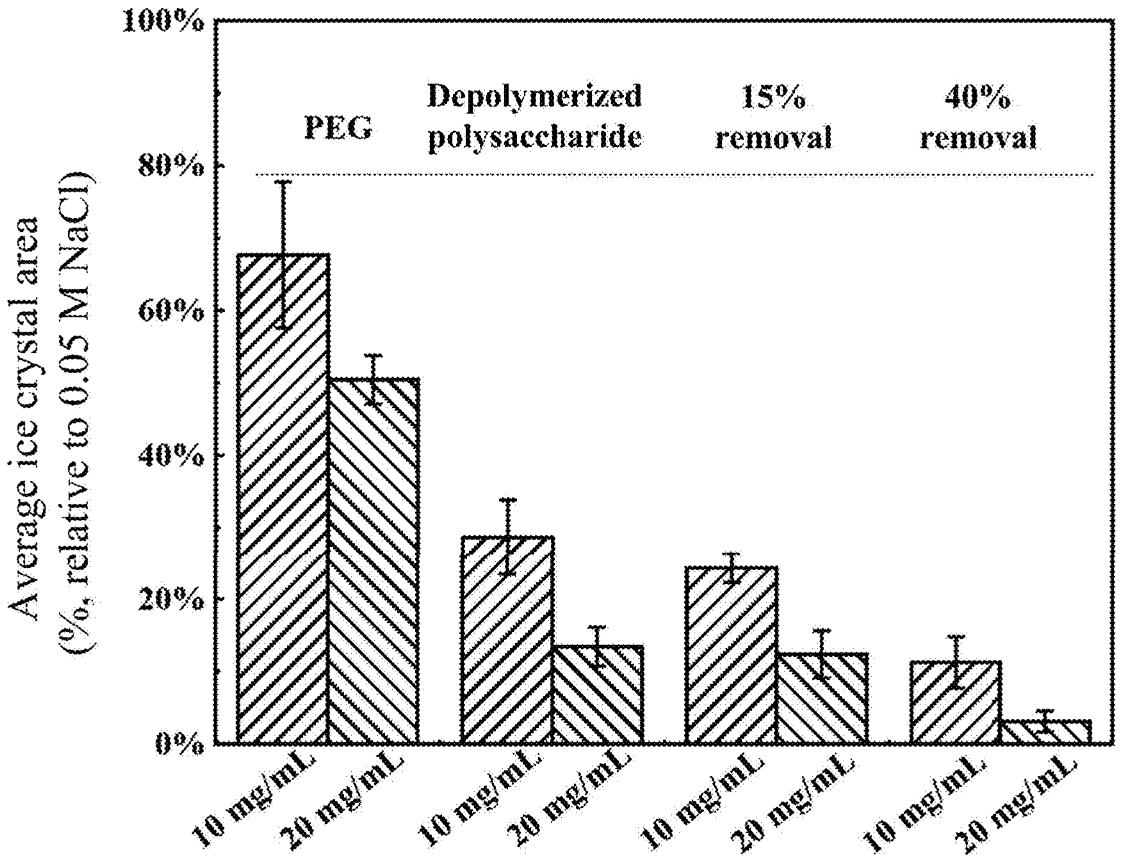
FIG. 14 shows statistical results of the ice recrystallization inhibition activity of the PEG negative control, the depolymerized TSP, and the reconstructed TSP in the 0.05 M NaCl system in Test Example 5.

As shown in FIG. 11 and FIG. 12, compared with natural TSP and depolymerized TSP, the ice recrystallization inhibition activity of the reconstructed TSP prepared by 40% side-chain removal was further significantly improved, and the area of inhibited ice crystals was only 6.23% that of the blank control at a concentration of 30 mg/mL.

Test Example 5

The area of inhibited ice crystals of the depolymerized TSP prepared in Example 2, the reconstructed TSP prepared in Example 3, and the reconstructed TSP prepared in Comparative Example 3 at different concentrations relative to the blank control group of 0.05 M NaCl solution was determined by the method in Test Example 1. The difference was that the solvent was a 0.05 M NaCl solution, and the results were shown in FIGS. 13A-D to FIG. 14. Depolymerized polysaccharide represented the depolymerized TSP prepared in Example 2, 40% removal represented the reconstructed TSP prepared in Example 3, and 15% removal represented the reconstructed TSP prepared in Comparative Example 3.

As shown in FIGS. 13A-13D and FIG. 14: changing the solution system of the ice recrystallization test, in the test of the 0.05 M NaCl solution system, the ice recrystallization inhibition activity of the reconstructed TSP was significantly improved, and the area of inhibited ice crystals of reconstructed TSP at 20 mg/mL concentration was only 3.5% that of the blank control.

According to the test results, it was concluded that the ice recrystallization inhibitor obtained by the present disclosure significantly improved ice recrystalization inhibition activity in different test systems. However, the actual effects of inhibiting ice crystal growth were different in different solution evaluation systems. In the system with low salt concentration, since the volume of the non-frozen phase formed after the solution was frozen was lower and the concentration effect was higher, the ice recrystalization inhibition was better.

From the above examples, it can be concluded that compared with natural TSP, the ice recrystallization inhibition activity of depolymerized TSP and reconstructed TSP provided by the present disclosure is significantly improved.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. An ice recrystallization inhibitor, comprising a reconstructed tamarind seed polysaccharide (TSP), wherein the reconstructed TSP has a fibrous supramolecular structure with a length of greater than 300 nm; wherein the reconstructed TSP has a number-average hydrodynamic diameter of 800-1200 nm; and wherein the reconstructed TSP is prepared by the following steps:

1) mixing a TSP aqueous solution with cellulase to allow cellulase enzymolysis to obtain a depolymerized TSP enzymolysis solution, 2) allowing the depolymerized TSP enzymolysis solution to have enzyme deactivation, conducting solid-liquid separation, and dialyzing an obtained supernatant at a cut-off molar mass of 14 kg/mol for 24-72 h to obtain a retentate, 3) subjecting the retentate to freeze-drying to obtain a depolymerized TSP, 4) redissolving the depolymerized TSP in water to obtain a depolymerized TSP aqueous solution, 5) mixing the depolymerized TSP aqueous solution with β-galactosidase to allow β-galactosidase enzymolysis to obtain a reconstructed TSP enzymolysis solution, and 6) after the β-galactosidase enzymolysis is completed, subjecting the reconstructed TSP enzymolysis solution to a post-treatment; and wherein the post-treatment comprises: allowing the reconstructed TSP enzymolysis solution to have enzyme deactivation, and subjecting an obtained mixture to ethanol precipitation to obtain a precipitated product; and 7) redissolving the precipitated product in water, and conducting freeze-drying to obtain the reconstructed TSP;

wherein the β-galactosidase is added at 1,500 U/L, and the β-galactosidase enzymolysis is conducted at 25° C. to 37° C. for 24 h to 48 h; the cellulase is added at 200 U/L; and the cellulase enzymolysis is conducted at a room temperature for 2 h to 4 h; the TSP aqueous solution has a concentration of 1 wt % to 3 wt % and a pH value of 5.0 to 5.5; and the depolymerized TSP aqueous solution has a concentration of 1 wt % to 3 wt % and a pH value of 4.5 to 5.0; and wherein the TSP aqueous solution comprises TSP with a weight-average molar mass of 1,000-2,500 kg/mol, and the TSP is a galactoxyloglucan derived from the seed of *Tamarindus indica* L.; and wherein the depolymerized TSP has a weight-average molar mass of 90 to 201 kg/mol.

2. The ice recrystallization inhibitor according to claim 1, wherein the ethanol precipitation of step 6) is performed at a volume ratio of the obtained mixture to ethanol of 1:3 or 1:4.

3. The ice recrystallization inhibitor according to claim 1, wherein the ethanol precipitation of step 6) is performed at a volume ratio of the obtained mixture to ethanol of 1:3.

4. The ice recrystallization inhibitor according to claim 1, wherein the dialysis in step 2) is performed for 72 h.

5. The ice recrystallization inhibitor according to claim 1, wherein the cellulase enzymolysis is conducted at room temperature for 4 h.

6. The ice recrystallization inhibitor according to claim 1, wherein the β-galactosidase enzymolysis is conducted at 37° C. for 48 h.

* * * * *